United States Patent
Klinge et al.

(10) Patent No.: US 6,686,369 B1
(45) Date of Patent: Feb. 3, 2004

(54) α-HYDRDROXYLIC ACID DERIVATIVES, THEIR PRODUCTION AND USE

(75) Inventors: Dagmar Klinge, Heidelberg (DE); Wilhelm Amberg, Friedrichsdorf (DE); Ernst Baumann, Dudenhofen (DE); Andreas Kling, Mannheim (DE); Hartmut Riechers, Neustadt (DE); Liliane Unger, Ludwigshafen (DE); Manfred Raschack, Weisenheim (DE); Stefan Hergenröder, Mainz (DE); Sabine Schult, Speyer (DE)

(73) Assignee: Abbott GmbH & Co., KG, Wiesbaden (DE)

(*) Notice: Subject to any disclaimer, the term of this patent is extended or adjusted under 35 U.S.C. 154(b) by 0 days.

(21) Appl. No.: 09/155,944

(22) PCT Filed: Apr. 4, 1997

(86) PCT No.: PCT/EP97/01688

§ 371 (c)(1),
(2), (4) Date: Oct. 8, 1998

(87) PCT Pub. No.: WO97/38981

PCT Pub. Date: Oct. 23, 1997

(30) Foreign Application Priority Data

Apr. 12, 1996 (DE) .......................................... 196 14 533

(51) Int. Cl.[7] ................... C07D 239/60; C07D 239/56; C07D 239/52; A61K 31/505; A61P 9/10
(52) U.S. Cl. ..................... 514/274; 544/315; 544/318; 544/319
(58) Field of Search ................................ 544/315, 318, 544/319; 514/274

(56) References Cited

U.S. PATENT DOCUMENTS

| | | | |
|---|---|---|---|
| 5,703,017 A | 12/1997 | Baumann et al. | 504/227 |
| 5,840,722 A | 11/1998 | Baumann et al. | 514/241 |

FOREIGN PATENT DOCUMENTS

| | | | |
|---|---|---|---|
| AU | 3 804 595 | | 5/1996 |
| DE | 40 35 758 | | 5/1992 |
| DE | 195 33 023 | * | 4/1996 |
| WO | WO 94/25442 | | 11/1994 |
| WO | WO 95/26716 | | 10/1995 |

OTHER PUBLICATIONS

Douglas, S. A., Clinical developments. of endothelin receptor antagonists TIBS 18, 408–413, 1997.*

* cited by examiner

Primary Examiner—Mukund J. Shah
Assistant Examiner—Venkataraman Balasubramanian
(74) Attorney, Agent, or Firm—Wood, Phillips, Katz, Clark & Mortimer

(57) ABSTRACT

The present invention relates to carboxylic acid derivatives of the formula

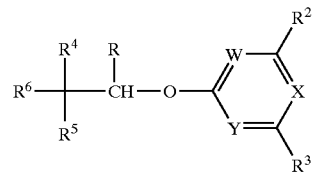

where the radicals have the meanings stated in the description, to the preparation of these compounds and to their use as drugs.

8 Claims, No Drawings

α-HYDRDROXYLIC ACID DERIVATIVES, THEIR PRODUCTION AND USE

The present invention relates to novel α-hydroxy acid derivatives, their preparation and use.

Endothelin is a peptide which is composed of 21 amino acids and is synthesized and released by the vascular endothelium. Endothelin exists in three isoforms, ET-1, ET-2 and ET-3. "Endothelin" or "ET" hereinafter signifies one or all isoforms of endothelin. Endothelin is a potent vasoconstrictor and has a great effect on vascular tone. It is known that this vasoconstriction is caused by the binding of endothelin to its receptor (Nature, 332, 411–415, 1988; FEBS Letters, 231, 440–444, 1988 and Biochem. Biophys. Res. Commun., 154, 868–875, 1988).

Increased or abormal [sic] release of endothelin causes a persistent contraction in peripheral, renal and cerebral blood vessels, which may lead to disorders. As reported in the literature, endothelin is involved in a number of disorders; these include hypertension, myocardial infarct, heart failure, kidney failure, pulmonary hypertension, Raynaud's syndrome, cerebral vasospasms, atherosclerosis, stroke, benign prostate hypertrophy and asthma (Japan J. Hyperteusion [sic] 12, 79 (1989), J. Vascular Med. Biology 2, 207 (1990), J. Am. Med. Association 264, 2868 (1990), Nature 344, 114 (1990), N. Engl. J. Med. 322, 205 (1989), N. Engl. J. Med. 328 1732 (1993), Nephton [sic] 66, 373 (1994), Stroke 25, 904 (1994), Nature 365, 759 (1993), J. Mol. Cell. Cardist. 27, A234 (1995), Cancer Research 56, 663 (1996)).

A compound having the formula A

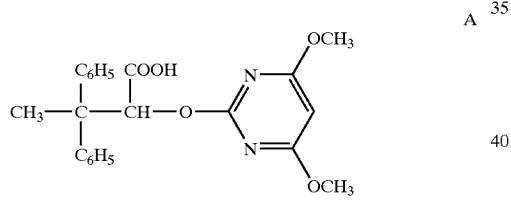

is mentioned in the European patent application with the file number P 44 36 851.8 (page 32, compound I-28). However, this compound cannot be prepared by the preparation process mentioned in this patent application.

Compounds of the formula B where $R^3$ can be, for example, phenyl, and $R^2$ and $R^4$ can be hydrogen or $C_1$–$C_4$-alkyl, are described in the European patent with the number 0 347 811 B1 as substances with herbicidal activity.

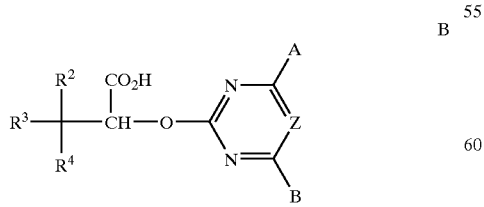

The invention relates to the α-hydroxy carboxylic acid derivatives of the formula I

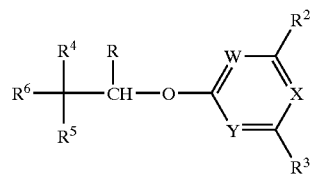

where R is formyl, a tetrazole [sic], nitrile [sic], a group COOH or a radical which can be hydrolyzed to COOH. R is, for example, a group

where $R^1$ has the following meanings:
a) hydrogen
b) a succinylimidoxy [sic] group
c) a 5-membered heteroaromatic system, such as pyrrolyl, pyrazolyl-[sic] imidazolyl and triazolyl, which is linked via a nitrogen atom and which may carry one or two halogen atoms or one or two $C_1$–$C_4$-akyl or one or two $C_1$–$C_4$-alkoxy groups;
d) $R^1$ furthermore a group

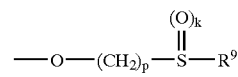

where k can assume the values 0, 1 and 2, p can assume the values 1, 2, 3 and 4, and $R^9$ is $C_1$–$C_4$-alkyl, $C_3$–$C_7$-cycloalkyl, $C_3$–$C_6$-alkenyl, $C_3$–$C_6$-alkynyl or unsubstituted or substituted phenyl which can be substituted by one or more, eg. one to three, of the following radicals: halogen, nitro, cyano, $C_1$–$C_4$-alkyl, $C_1$–$C_4$-haloalkyl, hydroxyl, $C_1$–$C_4$-alkoxy, $C_1$–$C_4$-alkylthio, mercapto, amino, $C_1$–$C_4$-alkylamino, $C_1$–$C_4$-dialkylamino;
e) $R^1$ furthermore a radical $OR^{10}$, where $R^{10}$ is:
hydrogen, the cation of an alkali metal such as lithium, sodium, potassium or the cation of an alkaline earth metal such as calcium, magnesium and barium, and physiologically tolerated alkylammonium ion or the ammonium ion;
$C_3$-$C_8$-cycloalkyl, such as cyclopropyl, cyclobutyl, cyclopentyl, cyclohexyl, cycloheptyl or cyclooctyl,
$C_1$–$C_8$-alkyl, in particular $C_1$–$C_4$-alkyl such as methyl, ethyl, n-propyl, isopropyl, n-butyl, isobutyl, tert-butyl;
$CH_2$-phenyl which can be substituted by one or more of the following radicals: halogen, nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $C_1$–$C_4$-alkylamino, $C_1$–$C_4$-dialkylamino,
a $C_3$–$C_6$-alkenyl or $C_3$–$C_6$-alkynyl group, it being possible for this group in turn to carry one to five halogen atoms;
$R^{10}$ can furthermore be a phenyl radical which can carry one to five halogen atoms and/or one to three of the following radicals: nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $C_1$–$C_4$-alkylamino, $C_1$–$C_4$-dialkylamino;
a 5-membered heteroaromatic system which is linked via a nitrogen atom and contains one to three nitrogen atoms, and which may carry one or two halogen atoms and/or one or two of the following radicals: $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. Particular mention may be made of: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3,4-dichloroimidazol-1-yl;

f) $R^1$ furthermore a radical

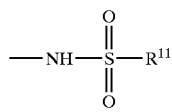

where $R^{11}$ is:

$C_1$–$C_4$-alkyl, $C_3$–$C_6$-alkenyl, $C_3$–$C_6$-alkynyl, $C_3$–$C_8$-cycloalkyl, it being possible for these radicals to carry a $C_1$–$C_4$-alkoxy, $C_1$–$C_4$-alkylthio and/or a phenyl radical;

phenyl which is unsubstituted or substituted, in particular as mentioned above;

g) $R^1$ a radical

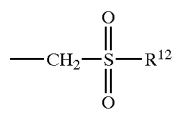

where $R^{12}$ has the same meanings as $R^{11}$;

h) $R^1$ can furthermore be

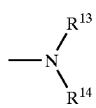

where $R^{13}$ and $R^{14}$ can be identical or different and have the following meanings:

hydrogen, $C_1$–$C_7$-alkyl, $C_3$–$C_7$-cycloalkyl, $C_3$–$C_7$-alkanyl [sic], $C_3$–$C_7$-alkynyl, benzyl, phenyl, unsubstituted or substituted, as described above or $R^{13}$ and $R^{14}$ together form a $C_4$–$C_7$-alkylene chain which is closed to a ring, is unsubstituted or substituted by $C_1$–$C_4$-alkyl, for example, and may contain a hetero atom, eg. oxygen, nitrogen or sulfur, such as —(CH$_2$)$_4$—, —(CH$_2$)$_5$—, —(CH$_2$)$_6$—, —(CH$_2$)$_7$—, —(CH$_2$)$_2$—O—(CH$_2$)$_2$—, —(CH$_2$)$_2$—S—(CH$_2$)$_2$—, —CH$_2$—NH—(CH$_2$)$_2$—, —(CH$_2$)$_2$—NH—(CH$_2$)$_2$—.

The other substituents have the following meanings:

W nitrogen or C—NO$_2$, furthermore W can be a CH group when one or more of the substituents $R^2$, $R^3$, $R^{15}$ and/or $R^{16}$ are a nitro group, or when X and/or Y are nitrogen;

$R^2$ is hydrogen, halogen, $C_1$–$C_4$-alkyl, $C_1$–$C_4$-haloalkyl, $C_1$–$C_4$-alkoxy, $C_1$–$C_4$-haloalkoxy, hydroxyl, mercapto, $C_1$–$C_4$-alkylthio, nitro, amino, $C_1$–$C_4$-alkylamino or $C_1$–$C_4$-dialkylamino, cyano, phenyl, optionally substituted once to three times by halogen, hydroxyl, amino, mono- or dialkyl ($C_1$–$C_3$)-amino, $C_1$–$C_3$-alkyl, $C_1$–$C_3$-alkoxy, mercapto or $C_1$–$C_3$-alkylthio, carboxyl, $C_1$–$C_3$-alkylcarboxyl;

or a five- or six-membered heteroaromatic system containing one to three nitrogen atoms and/or one sulfur or oxygen atom, which carries one to three substituents as described above;

$R^2$ can furthermore form, with the adjacent carbon atom and X, a 5- or 6-membered alkylene or alkylidene [sic] ring in each of which one or two carbon atoms can be replaced by a hetero atom such as nitrogen, sulfur or oxygen, and which can be substituted once to three times by the following radicals: halogen, nitro, cyano, hydroxyl, mercapto, $C_1$–$C_3$-alkyl, $C_1$–$C_3$-haloalkyl, $C_1$–$C_3$-alkoxy, $C_1$–$C_3$-alkylthio, amino, $C_1$–$C_3$-alkylamino, $C_1$–$C_3$-dialkylamino;

X is nitrogen or $CR^{15}$ where $R^{15}$ is hydrogen, nitro, $C_1$–$C_5$-alkyl or $C_2$–$C_5$-alkenyl, optionally substituted once or twice by hydroxyl, carboxyl or phenyl, which in turn can be substituted by $C_1$–$C_3$-alkyl, hydroxyl or carboxyl; $C_1$–$C_6$-alkoxy, $C_1$–$C_6$-alkylthio, phenyl, hydroxyl, mercapto, nitro, amino, $C_1$–$C_4$-alkylamino, $C_1$–$C_4$-dialkylamino, cyano or carboxyl;

it is furthermore possible for $CR^{15}$ to be linked to $R^2$ to give a 5- or 6-membered ring as described above, or $CR^{15}$ can form with $R^3$ and its adjacent carbon atom a 5- or 6-membered alkylene or alkylidene [sic] ring in each of which one or two carbon atoms can be replaced by nitrogen, oxygen or sulfur, and the 5- or 6-membered ring may optionally be substituted once to three times by the following radicals:

halogen, nitro, cyano, hydroxyl, mercapto, $C_1$–$C_3$-alkyl, $C_1$–$C_3$-haloalkyl, $C_1$–$C_3$-alkoxy, $C_1$–$C_3$-alkylthio, amino, $C_1$–$C_3$-alkylamino, $C_1$–$C_3$-dialkylamino or carboxyl; nitrogen in the 5-membered ring may also be substituted by a formyl or acetyl group;

$R^3$ can have the same meanings as $R^2$, $R^2$ and $R^3$ can be identical or different; it is furthermore possible for $R^3$ to form with the adjacent carbon atom and with X a 5- or 6-membered ring as described above; it is furthermore possible for $R^3$ to form together with the adjacent carbon atom and Y a 5- or 6-membered alkylene or alkylidene [sic] ring in each of which one or two carbon atoms can be replaced by nitrogen, oxygen or sulfur; the 5- or 6-membered ring may optionally be substituted once to three times by the following radicals:

halogen, nitro, cyano, hydroxyl, mercapto, $C_1$–$C_3$-alkyl, $C_1$–$C_3$-haloalkyl, $C_1$–$C_3$-alkoxy, $C_1$–$C_3$-alkylthio, amino, $C_1$–$C_3$-alkylamino, $C_1$–$C_3$-dialkylamino or carboxyl; nitrogen in the 5-membered ring may also be substituted by a formyl or acetyl group;

Y is nitrogen or $CR^{16}$ where $R^{16}$ is hydrogen, $C_1$–$C_5$-alkyl, $C_1$–$C_5$-alkoxy, $C_1$–$C_5$-alkylthio, nitro, phenyl, hydroxyl, halogen, cyano, amino, $C_1$–$C_4$-alkylamino, $C_1$–$C_4$-dialkylamino, mercapto or carboxyl, or $CR^{16}$ forms together with $R^3$ and its adjacent carbon atom a 5- or 6-membered ring as described above;

$R^4$ is phenyl, naphthyl, dihydro- or tetrahydronaphthyl, which can be substituted by one or more of the following radicals: halogen, nitro, cyano, hydroxyl, $C_1$–$C_4$-alkyl, $C_1$–$C_4$-haloalkyl, $C_1$–$C_4$-alkoxy, $C_1$–$C_4$-haloalkoxy, phenoxy, phenyl, $C_1$–$C_4$-alkylthio, amino, $C_1$–$C_4$-alkylamino or $C_1$–$C_4$-dialkylamino, it being possible for two radicals on adjacent carbon atoms to form, together with the latter, a five- or six-membered ring which is linked by an alkylene or alkylidene [sic] group and in which one or more methylene or methylidene [sic] groups can be replaced by oxygen, such as —(CH$_2$)$_3$—, —(CH$_2$)$_4$—, —CH═CH—O—, —O—CH$_2$—O—, —O—(CH$_2$)$_2$—O—, —CH═CH—CH$_2$— or —O—CH═CH—O—;

R$^4$ can be, for example, the following radicals:

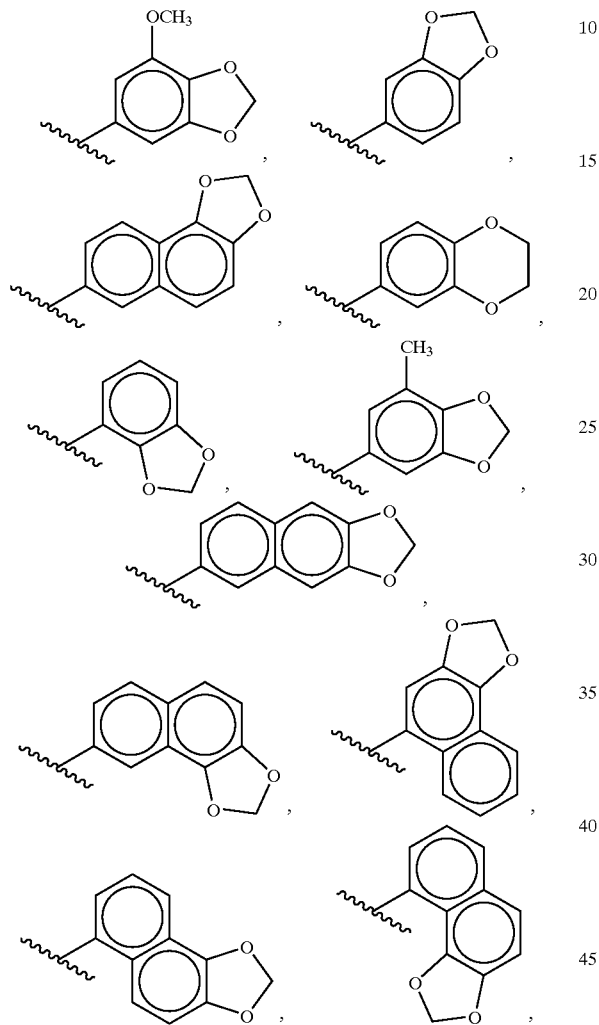

R$^4$ can furthermore be a five- or six-membered heteroaromatic system which contains a nitrogen, sulfur or oxygen atom and which can carry one or two of the following radicals: halogen, cyano, nitro, C$_1$–C$_4$-alkyl, C$_1$–C$_4$-haloalkyl, C$_1$–C$_4$-alkoxy, phenoxy, C$_1$–C$_4$-alkylthio, C$_1$–C$_4$-alkylamino or C$_1$–C$_4$-dialkylamino;

in addition, R$^4$ and R$^5$ can be phenyl groups which are connected together in the ortho positions by a direct linkage, a methylene, ethylene or ethenylene group, an oxygen or sulfur atom or an SO$_2$—, NH— or N-alkyl group;

R$^5$ can have the same meanings as R$^4$, it being possible for R$^4$ and R$^5$ to be identical or different;

R$^6$ is hydrogen, C$_1$–C$_8$-alkyl, C$_2$–C$_8$-alkenyl or C$_3$–C$_8$-alkynyl, it being possible for each of these radicals to be substituted one or more times by: halogen, nitro, cyano, C$_1$–C$_4$-alkoxy, hydroxyl, C$_1$–C$_4$-alkylthio, mercapto, C$_1$–C$_4$-haloalkoxy, carboxyl, C$_1$–C$_4$-alkylcarboxyl, C$_1$–C$_4$-alkylcarbonyl, amino, C$_1$–C$_4$-alkylamino, C$_1$–C$_4$-dialkylamino or phenyl, or naphthyl which can in turn be substituted one or more times by: halogen, nitro, cyano, hydroxyl, C$_1$–C$_4$-alkoxy, C$_1$–C$_4$-alkyl, C$_1$–C$_4$-haloalkyl, C$_1$–C$_4$-haloalkoxy, mercapto, C$_1$–C$_4$-alkylthio, amino, C$_1$–C$_4$-alkylamino, C$_1$–C$_4$-dialkylamino or phenoxy, R$^6$ is furthermore C$_1$–C$_4$-alkyl which is substituted by phenoxymethyl in which the phenyl group can be substituted once or twice by halogen, methyl or methoxy;

R$^6$ is furthermore also a C$_1$–C$_8$-alkyl, C$_3$–C$_8$-alkenyl or C$_3$–C$_8$-alkynyl chain which is substituted by of the following radicals:

a five- or six-membered heteroaromatic system which contains one to three nitrogen atoms and/or one sulfur or oxygen atom and which can carry one to four halogen atoms and/or one or two of the following radicals: C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, phenyl, phenoxy or phenylcarbonyl, it being possible for the phenyl radicals in turn to carry one to five halogen atoms and/or one to three of the following radicals: C$_1$–C$_4$-alkyl, C$_1$–C$_4$-haloalkyl, C$_1$–C$_4$-alkoxy, C$_1$–C$_4$-haloalkoxy and/or C$_1$–C$_4$-alkylthio;

or one of the following radicals:

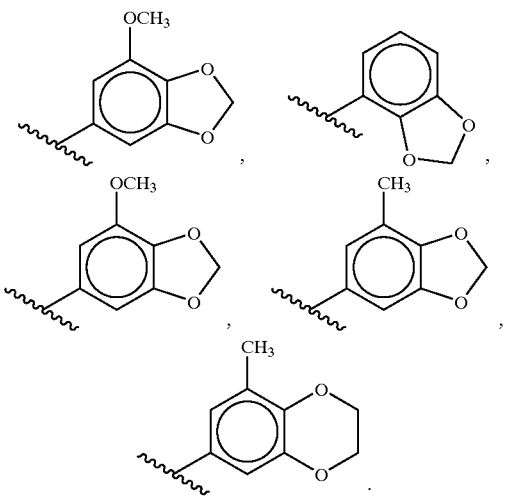

The compounds and the intermediates II for preparing them may have one or more asymmetrically substituted carbon atoms. Such compounds may be in the form of pure enantiomers or pure diastereomers or of a mixture thereof. It is preferred to use an enantiomerically pure compound as active substance.

The invention furthermore relates to the use of the above-mentioned amino acid derivatives for producing drugs, in particular for producing inhibitors for endothelin receptors.

The compounds according to the invention are prepared by reacting a hydroxy acid derivative II in which the substituents have the stated meaning with compounds of the general formula III,

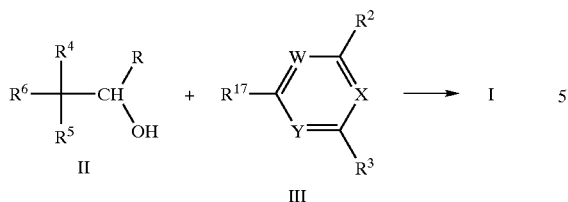

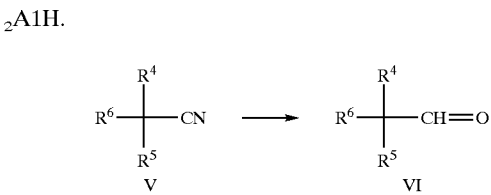

where $R^{17}$ is halogen or $R^{18}$ —$SO_2$—, where $R^{18}$ can be $C_1$–$C_4$-alkyl, $C_1$–$C_4$-haloalkyl or phenyl.

The reaction preferably takes place in an inert diluent with the addition of a suitable base, ie. a base which deprotinates the intermediate II, at a temperature in the range from room temperature to the boiling point of the solvent.

Examples of such solvents or diluents are water, aliphatic, alicyclic and aromatic hydrocarbons, which may be chlorinated, such as hexane, cyclohexane, petroleum ether, naphtha, benzene, toluene, xylene, methylene chloride, chloroform, carbon tetrachoride, ethylene chloride and trichloroethylene, ethers such as diisopropyl ether, dibutyl ether, propylene oxide, dioxane and tetrahydrofuran, ketones such as acetone, methyl ethyl ketone, methyl isopropyl ketone and methyl isobutyl ketone, nitriles such as acetonitrile and propionitrile, alcohols such as methanol, ethanol, isopropanol, butanol and ethylene glycol, esters such as ethyl acetate and amyl acetate, amides such as dimethylformamide and dimethylacetamide, sulfoxides and sulfones, such as dimethyl sulfoxide and sulfolane, and bases such as pyridine, N-methylpyrrolidone, cyclic ureas such as 1,3-dimethyl-2-imidazolidinone and 1,3-dimethyl-3,4,5,6-tetrahydro-2(1H)-pyrimidinone. The reaction is preferably carried out at a temperature in the range from 0° C. to the boiling point of the solvent or mixture of solvents.

It is possible to use as base an alkali metal or alkaline earth metal hydride such as sodium hydride, potassium hydride or calcium hydride, a carbonate such as alkali metal carbonate, eg. sodium or potassium carbonate, an alkali metal or alkaline earth metal hydroxide such as sodium or potassium hydroxide, an organometallic compound such as butyllithium or an alkali metal amide such as lithium diisopropylamide or lithium amide, or tertiary amines, eg. triethylamine, pyridine, 4-N,N-dimethylaminopyridine, imidazole or diazobicycloundecane [sic].

The invention also relates to compounds of the formula II which are unknown. They can be prepared in a known manner.

For example, compounds of the formula II can be prepared by converting a nitrile of the formula IV, by alkylation with the aid of a base and of a compound $R^6$—K, into a nitrile V

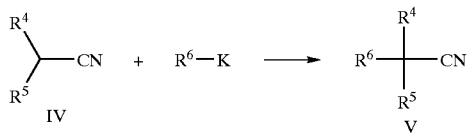

as described, for example, in Ca. J. of Chem. 47 (1969) 1587 et seq., where K is a leaving group such as halogen, tosylate, mesylate or triflate.

The nitrites V are then reduced to aldehydes VI as described in Synth. Comm. 19 (1989) 355 et seq. or J. Am. Chem. Soc. 107 (1985) 4577 et seq. Reducing agents which can be used are metal hydrides such as $LiAlH_4$ or (n-Bu)$_2AlH$.

The aldehydes VI are converted by known methods (as described, for example, in Chem. Pharm. Bull. 37 (1989) 2570–2) into the corresponding cyanohydrins VII:

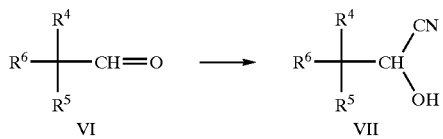

Cyanohydrins VII can be converted by hydrolysis, for example with aqueous HCl, or by the Pinner method with HCl gas in alcohol $R^{10}OH$, into α-hydroxy carboxylic acid derivatives II where

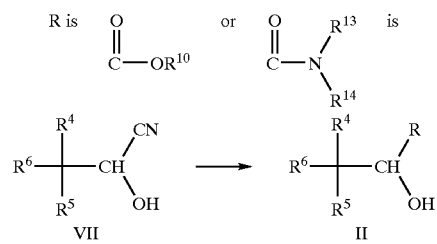

Compounds II can also be prepared by diazotizing an amino acid derivative VIII by known methods, eg. with sodium nitrite and aqueous sulfuric acid, and hydrolyzing to the hydroxy acid derivative II as described, for example, in Synthesis (1987), 479–80.

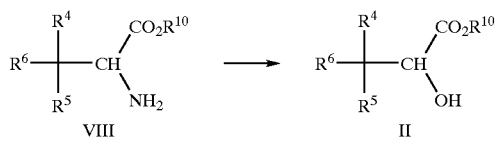

Amino acid derivatives VIII can be prepared, for example, in a Strecker reaction from the aldehydes VI, eg. as disclosed in Angew. Chem. Int. Ed. 26 (1987), 557 et seq.

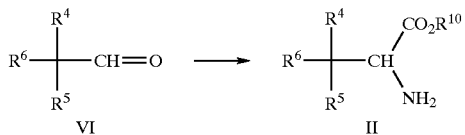

In addition, compounds VIII can be prepared by reacting a compound IX with a Grignard compound X, and hydrolyzing the product XI with acid to VIII, similar to the description in Liebigs Ann. (1977) 1174–1182:

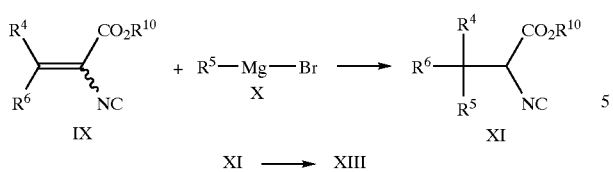

Compounds II can furthermore be synthesized by electrophilic oxidation of carboxylic acid derivatives XII, eg. with oxygen after deprotonation, as described in Tetrahedron Letters 21 (1975) 1731–4, or with Davis' reagent

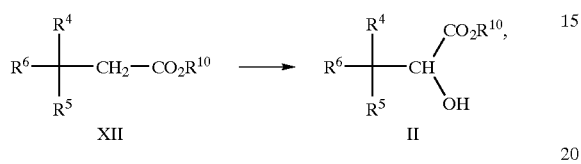

as described in J. Org. Chem. 47 (1982) 1775–77.

Compounds XII can be prepared by reacting a suitable phosphonate compound XIII with a carbonyl compound XIV in a Wittig-Horner reaction to give the unsaturated compound XV.

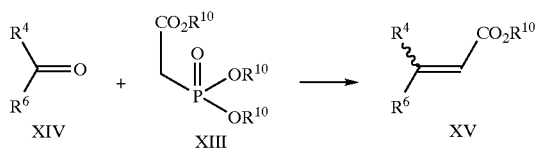

Compound XV can then be converted by a method from Chem. Ber. 64 (1931) 1493 et seq. with $R^5$—H in the presence of a Friedel-Crafts catalyst such as aluminum trichloride into the carboxylic acid derivative XVI.

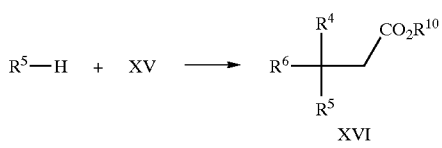

Compounds I can also be prepared by reacting cyanohydrins VII with compounds III to give nitriles XVII.

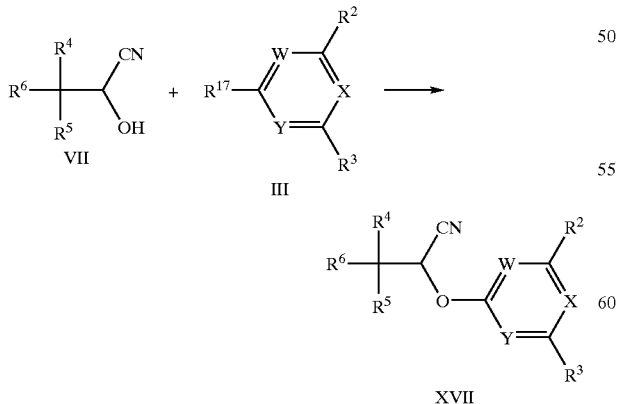

The reaction preferably takes place in an inert solvent with the addition of a suitable base as described previously.

Compounds XVII can then be converted in a known manner, for example by reaction with acids such as hydrochloric acid or sulfuric acid, with or without addition of an alcohol into compounds of type I.

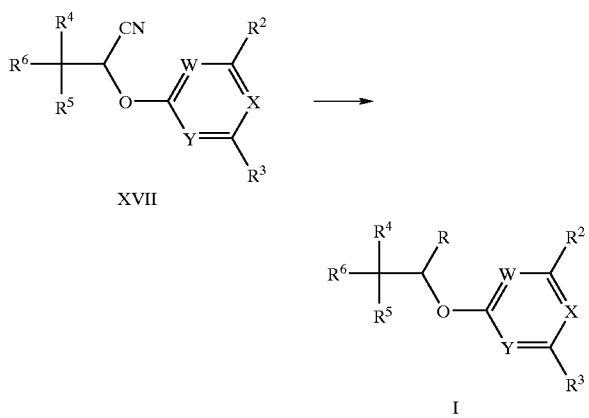

Compounds of the formula I can be obtained in enantiomerically pure form by starting from enantiomeric compounds II, which can be prepared by classical racemate resolution or by enantioselective syntheses (such as, for example, Pure Appl. Chem., 55 (1983) 1799 et seq.; Helv. Chim. Acta, 71 (1988) 224 et seq.; J. Am. Chem. Soc, 110 (1988) 1547–1557; Chem. Eng. News (1989) 25–27) in enantiomerically pure and, where appropriate, diastereomerically pure form, and reacting these compounds II with III as described above. Another possibility for obtaining enantiomerically pure compounds of the formula I is classical racemate resolution of racemic or diastereomeric compounds I with suitable enantiomerically pure bases such as brucine, strychnine, quinine, quinidine, chinchonidine [sic], chinchonine [sic], yohimbine, morphine, dehydroabietylamine, ephedrine (−), (+), deoxyephedrine (+), (−), threo-2-amino-1-(p-nitrophenyl)-1,3-propanediol (+), (−), threo-2-(N,N-dimethylamino)-1-(p-nitrophenyl)-1,3-propanediol (+), (−) threo-2-amino-1-phenyl-1,3-propanediol (+), (−), α-methylbenzylamine (+), (−), α-(1-naphthyl)ethylamine (+), (−), α-(2-naphthyl)ethylamine (+), (−), aminomethylpinone, N,N-dimethyl-1-phenylethylamine, N-methyl-1-phenylethylamine, 4-nitrophenylethylamine, pseudoephedrine, norephedrine, norpseudoephedrine, amino acid derivatives and peptide derivatives.

Preferred compounds of the formula I, both as pure enantiomers and pure diastereomers or as mixture thereof, are those where the substituents have the following meanings:

R a carboxylic acid, a carboxylic acid salt or a group which can be hydrolyzed to a carboxylic acid, as described above.

W nitrogen or C—$NO_2$;

X nitrogen or $CR^{15}$ where $R^{15}$ is hydrogen, nitro, $C_1$–$C_5$-alkyl or $C_1$–$C_5$-alkenyl, optionally substituted by hydroxyl, carboxyl or phenyl, which can in turn be substituted by $C_1$–$C_3$-alkyl, hydroxyl or carboxyl; $C_1$–$C_4$-alkoxy, $C_1$–$C_4$-alkylthio, hydroxyl, nitro, amino, cyano or carboxyl, or $CR^{15}$ forms with $R^2$ and the adjacent carbon atom a 5- or 6-membered alkylene or alkylidene [sic] ring in which one or two carbon atoms can be replaced by a hetero atom such as nitrogen, oxygen or sulfur, and which can be substituted once or twice by a $C_1$–$C_3$-alkyl or $C_1$–$C_3$-alkoxy group; nitrogen in the 5-membered ring may additionally be substituted by a CHO or COCH$_3$ group;

$R^2$ hydrogen, halogen, $C_1$–$C_4$-alkyl, $C_1$–$C_4$-haloalkyl, $C_1$–$C_4$-alkoxy, $C_1$–$C_4$-alkylthio, nitro, amino, methylamino, dimethylamino or cyano; $R^2$ can furthermore form with the adjacent carbon atom and X a 5- or 6-membered ring as described above;

$R^3$ hydrogen, halogen, $C_1$–$C_4$-alkyl, $C_1$–$C_4$-alkoxy, $C_1$–$C_4$-haloalkyl, $C_1$–$C_4$-alkylthio, nitro, amino, methylamino, dimethylamino or cyano; $R^3$ can furthermore form with the adjacent carbon atom and Y a 5- or 6-membered alkylene or alkylidene [sic] ring in which one or two carbon atoms can be replaced by nitrogen, oxygen or sulfur and which can be substituted once or twice by a $C_1$–$C_3$-alkyl or $C_1$–$C_3$-alkoxy group; nitrogen in the 5-membered ring may also be substituted by a formyl or acetyl group;

Y nitrogen or $CR^{16}$ where $R^{16}$ is hydrogen, $C_1$–$C_3$-alkyl, $C_1$–$C_3$-alkoxy, $C_1$–$C_3$-alkylthio, nitro, halogen, cyano, amino, methylamino, dimethylamino or carboxyl, or if $CR^{16}$ forms together with $R^3$ and its adjacent carbon atom a 5- or 6-membered ring as described above;

$R^4$ is phenyl or naphthyl which can be substituted by one or more of the following radicals:
halogen, hydroxyl, $C_1$–$C_4$-alkyl, $C_1$–$C_4$-haloalkyl, $C_1$–$C_4$-alkoxy, $C_1$–$C_4$-alkylthio or phenyl, and the aromatic system may furthermore be substituted, exclusively or in addition to the abovementioned radicals, by two radicals on adjacent carbon atoms which together represent a 1,3-dioxomethylene [sic] or 1,4-dioxoethylene [sic] group and form with the adjacent carbon atoms a 5- or 6-membered ring respectively;
in addition, $R^4$ and $R^5$ can be phenyl groups which are connected together in ortho positions by a direct linkage, a methylene, ethylene or ethenylene group, or an oxygen or sulfur atom;

$R^5$ can have the same meanings as $R^4$, it being possible for $R^4$ and $R^5$ to be identical or different;

$R^6$ is hydrogen, $C_1$–$C_6$-alkyl, $C_2$–$C_6$-alkenyl or $C_3$–$C_6$-alkynyl, it being possible for each of these radicals to be substituted once to three times by:
halogen, cyano, $C_1$–$C_3$-alkoxy, hydroxyl, $C_1$–$C_3$-alkylthio, mercapto, $C_1$–$C_3$-haloalkoxy, carboxyl, $C_1$–$C_3$-alkylcarboxyl or phenyl, or naphthyl which can likewise be substituted once to three times by the following radicals:
halogen, cyano, hydroxyl, $C_1$–$C_3$-alkoxy, $C_1$–$C_4$-alkyl, $C_1$–$C_4$-haloalkyl, $C_1$–$C_3$-haloalkoxy, mercapto, $C_1$–$C_3$-alkylthio, phenyl or phenoxy, or, exclusively or in addition to the abovementioned radicals, two radicals on adjacent carbon atoms may together represent a 1,3-dioxomethylene [sic] or 1,4-dioxoethylene [sic] group, and $R^6$ can furthermore be a phenylmethoxymethyl, -ethyl or -propyl group in which the phenyl group is substituted by methyl, methoxy or halogen.

Particularly preferred compounds of the formula I, both as pure enantiomers and pure diastereomers or as mixture thereof, are those in which the substituents have the following meanings:

R a carboxylic acid, a carboxylic acid salt or a group which can be hydrolyzed to a carboxylic acid, as described above;

W nitrogen;

X nitrogen or $CR^{15}$ where $R^{15}$ is hydrogen, $C_1$–$C_5$-alkyl or $C_1$–$C_5$-alkenyl, optionally substituted by hydroxyl, carboxyl or phenyl, which can in turn be substituted by $C_1$–$C_3$-alkyl, hydroxyl or carboxyl, $C_1$–$C_3$-alkoxy, $C_1$–$C_3$-alkylthio, hydroxyl, cyano or carboxyl, or $CR^{15}$ forms with $R^3$ and the adjacent carbon atom a 5- or 6-membered alkylene or alkylidene [sic] ring in which one carbon atom can be replaced by oxygen and which can be substituted by a methoxy or methyl group;

for example, the 5- or 6-membered alkylene and alkylidene [sic] ring may have the following structures:

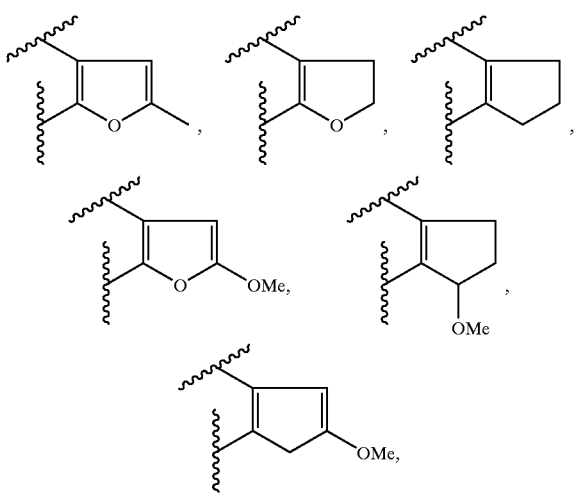

$R^2$ hydrogen, chlorine, methyl, ethyl, trifluoromethyl, nitro, methoxy, ethoxy, methylmercapto, amino, dimethylamino, methylamino; $R^2$ may furthermore form with the adjacent carbon atom and X a 5- or 6-membered ring as described above;

$R^3$ hydrogen, chlorine, methyl, ethyl, trifluoromethyl, nitro, methoxy, ethoxy, methylmercapto, amino, methylamino or dimethylamino;

$R^3$ may furthermore form with Y a 5- or 6-membered alkylene or alkylidene [sic] ring in which one or two carbon atoms may be replaced by nitrogen or oxygen, and which can be substituted by a methyl or methoxy group; examples of such alkylene or alkylidene [sic] rings are:

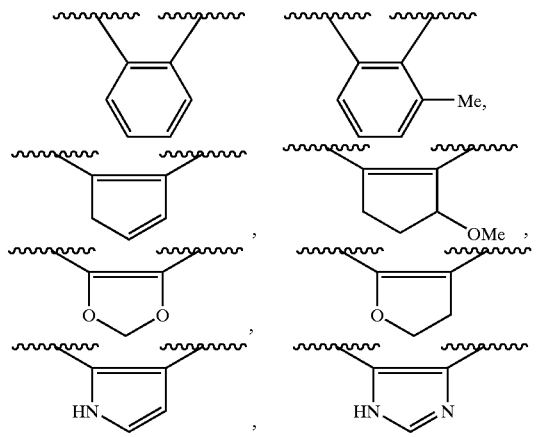

Y nitrogen or $CR^{16}$ where $R^{16}$ is hydrogen, nitro, methyl, ethyl, chlorine or cyano, or $CR^{16}$ forms with $R^3$ and its adjacent carbon atom a 5- or 6-membered ring as described above;

R⁴ is phenyl which carries one or two of the following radicals: halogen, hydroxyl, methoxy, ethoxy, $C_1$–$C_3$-alkyl, trifluoromethyl, methylmercapto, ethylmercapto or phenyl; it is furthermore possible for two substituents to represent a dioxomethylene [sic] group, exclusively or in addition to other substituents; examples of such groups representing R⁴ are:

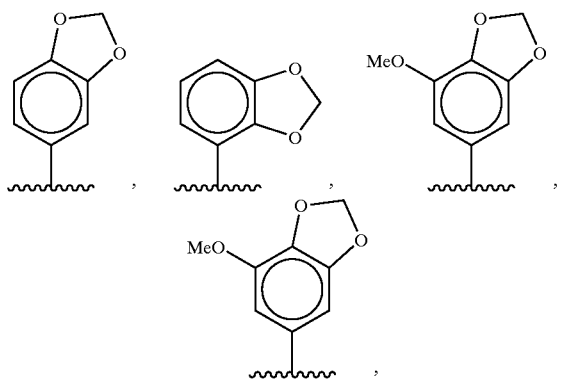

in addition, R⁴ and R⁵ can be phenyl group [sic] which are connected together in ortho positions by a direct linkage, a methylene or ethylene group;

R⁵ can have the same meanings as R⁴, and R⁴ and R⁵ can be identical or different;

R⁶ is hydrogen, $C_1$–$C_6$-alkyl or $C_3$–$C_6$-alkenyl, it being possible for each of these radicals to be substituted once or twice by:
chlorine, cyano, hydroxyl, carboxyl, methoxy, ethoxy, methylmercapto, methylcarboxyl, phenylmethoxy, p-methylphenylmethoxy, p-methoxyphenylmethoxy, p-fluorophenylmethoxy, or phenyl which can be substituted once or twice by the following radicals:
chlorine, fluorine, cyano, hydroxyl, methoxy, ethoxy, trifluoromethyl, trifluoromethoxy, methylmercapto, phenyl or phenoxy, or, exclusively or in addition to the abovementioned radicals, two radicals on adjacent carbon atoms may represent a 1,3-dioxomethylene [sic] group.

The compounds of the present invention offer a novel potential therapy for the treatment of hypertension, pulmonary hypertension, myocardial infarct, angina pectoris, acute kidney failure, renal insufficiency, cerebral vasospasms, cerebral ischemia, subarachnoid hemorrhages, migraine, asthma, atherosclerosis, endotoxic shock, endotoxin-induced organ failure, intravascular coagulation, restenosis after angioplasty, benign prostate hyperplasia, kidney failure caused by ischemia and by intoxication, and hypertension, and of cancers, in particular prostate cancer and skin cancer.

The good effect of the compounds can be shown in the following experiments:

Receptor Binding Studies

For binding studies, cloned human $ET_A$ receptor-expressing CHO cells and guinea-pig cerebellar membranes with >60% $ET_B$ relative to $ET_A$ receptors were employed.

Membrane Preparation

The $ET_A$ receptor-expressing CHO cells were grown in $F_{12}$ medium with 10% fetal calf serum, 1% glutamine, 100 U/ml penicillin and 0.2% streptomycin (Gibco BRL, Gaithersburg, Md., USA). After 48 h, the cells were washed with PBS and incubated with 0.05% trypsin-containing PBS for 5 min. After neutralization with $F_{12}$ medium, the cells were collected by centrifugation at 300×g. For cell lysis, the pellet was briefly washed with lysis buffer (5 mM Tris-HCl, pH 7.4 with 10% glycerol) and then incubated at a concentration of $10^7$ cells/ml of lysis buffer at 4° C. for 30 min. The membranes were centrifuged at 20,000×g for 10 min, and the pellet was stored in liquid nitrogen.

Guinea-pig cerebella were homogenized in a Potter-Elvejhem homogenizer and obtained by differential centrifugation at 1000×g for 10 min and repeated centrifugation of the supernatant at 20,000×g for 10 min.

Binding Assays

For the $ET_A$ and $ET_B$ receptor binding assays, the membranes were suspended in incubation buffer (50 mM Tris-HCl, pH 7.4 with 5 mM $MnCl_2$, 40 μg/ml bacitracin and 0.2% BSA) at a concentration of 50 μg of protein per assay mixture and incubated at 25° C. with 25 pM [125I [sic]]-$ET_1$ ($ET_A$ receptor assay) or 25 pM [125I [sic]]-$RZ_3$ ($ET_B$ receptor assay) in the presence and absence of test substance. The nonspecific binding was determined with $10^{-7}$ M $ET_1$. Filtration through GF/B glass fiber filters (Whatman, England) in a Skatron cell collector (Skatron, Lier, Norway) after 30 min separated the free and the bound radioligand, and the filters were washed with ice-cold Tris-HCl buffer, pH 7.4 with 0.2% BSA. The radioactivity collected on the filters was quantified using a Packard 2200 CA liquid scintillation counter.

Functional in vitro assay system to search for endothelin receptor (subtype A) antagonists This assay system is a functional, cell-based assay for endothelin receptors. Certain cell s show, when they are stimulated with endothelin 1 (ET1), an increase in the intracellular calcium concentration. This increase can be measured in intact cells which have been loaded with calcium-sensitive dyes.

1-Fibroblasts isolated from rats in which an endogenous endothelin receptor of the A subtype has been detected were loaded with the fluorescent dye Fura 2-an as follows: after trypsinization, the cells were resuspended in buffer A (120 mM NaCl, 5 mm KCl, 1.5 mM $MgCl_2$, 1 mM $CaCl_2$, 25 mM HEPES, 10 mM glucose, pH 7.4) to a density of $2 \times 10^6$/ml and incubated at 37° C. in the dark with Fura 2-am (2 μM), Pluronics [sic] F-127 (0.04%) and DMSO (0.2%) for 30 min. The cells were then washed twice with buffer A and resuspended at $2 \times 10^6$/ml.

The fluorescent signal with Ex/Em 380/510 from $2 \times 10^5$ cells per ml was continuously recorded at 30° C. The test substances and, after incubation for 3 min, ET1 were [lacuna] to the cells, the maximum change in fluorescence was determined. The response of the cells to ET1 without previous addition of a test substance served as control and was set equal to 100%.

In Vivo Testing of ET Antagonists

Male SD rats weighing 250–300 g were anesthetized with amobarbital, artificially ventilated, vagotomized and pithed. The carotid artery and jugular vein were cathetized [sic].

In control animals, intravenous administration of 1 μg/kg ET1 leads to a distinct rise in blood pressure which persists for a lengthy period.

The test compounds were injected i.v. (1 ml/kg) into the test animals 5 min before administration of ET1. To determine the ET-antagonistic properties, the rise in blood pressure in the test animals was compared with that in the control animals.

"Sudden Death" Induced by Endothelin-1 in Mice

The principle of the test comprises prevention of the sudden heart death caused in mice by endothelin, probably owing to constriction of the coronary vessels, by pretreatment with endothelin receptor antagonists. Intravenous injection of 10 nmol/kg endothelin in a volume of 5 ml/kg of body weight is followed within a few minutes by the death of the animals.

The lethal endothelin-1 dose is checked on each occasion on a small group of animals. If the test substance is administered intravenously, usually the endothelin-1 injection which was lethal in the reference group takes place 5 min thereafter. With other modes of administration, the times between administrations are longer, where appropriate up to several hours.

The survival rate is recorded and doses which effectively protect 50% of the animals from endothelin-induced heart death for 24 h or longer (ED 50) are determined.

Functional Test on Vessels for Endothelin Receptor Antagonists

Firstly a contraction is induced with $K^+$ in segments of rabbit aorta after an initial tension of 2 g and a relaxation time of 1 h in Krebs-Henseleit solution at 37° C. and a pH of 7.3–7.4. After washing out, an endothelin dose-effect plot is constructed up to the maximum.

Potential endothelin antagonists are administered to other preparations of the same vessel 15 min before the start of the endothelin dose-effect plot. The effects of endothelin are calculated as a % of the $K^+$ contraction. With effective endothelin antagonists, the endothelin dose-effect plot is shifted to the right.

The compounds according to the invention can be administered orally or parenterally (subcutaneously, intravenously, intramuscularly, intraperotoneally [sic]) in a conventional way. Administration can also take place with vapors or sprays through the nasopharyngeal space.

The dosage depends on the age, condition and weight of the patient and on the mode of administration. As a rule, the daily dose of active substance is from about 0.5 to 50 mg/kg of body weight on oral administration and from about 0.1 to 10 mg/kg of body weight on parenteral administration.

The novel compounds can be used in conventional solid or liquid pharmaceutical forms, eg. as uncoated or (film-) coated tablets, capsules, powders, granules, suppositories, solutions, ointments, creams or sprays. These are produced in a conventional way. For this purpose, the active substances can be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1991). The forms obtained in this way normally contain from 0.1 to 90% by weight of active substance.

The invention further relates to the combination of compounds of the formula I with inhibitors of the renin-angiotensin system (RAS). RAS inhibitors are disclosed in, for example, EP 634 175.

The combinations according to the invention are suitable for treating disorders for which compounds of the formula I also show efficacy on their own, especially for treating hypertension and chronic heart failure.

The invention further relates to the use of a structural fragment of the formula (A)

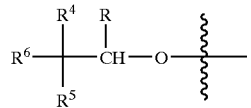

(A)

where R—$R^6$ have the meanings stated above for compounds of the formula I, as structural element in a pharmaceutically active compound with endothelin receptor-antagonizing action.

Synthesis Examples

Example 1

2,2-Diphenylpropional [sic]

50.0 g (0.241 mol) of 2,2-diphenylpropionitrile were dissolved in 200 ml of absolute diethyl ether, and 74.2 ml of a one-molar solution of $LiAlH_4$ in ether were added dropwise. The mixture was then refluxed for one hour and stirred at room temperature for 16 hours.

Then 29 ml of water were added, the organic phase was separated off, and the aqueous phase was extracted with ether. The combined organic phases were dried with $MgSO_4$, and the solvent was stripped off under reduced pressure. 52.1 g of oily crude product were obtained and were immediately reacted further.

Example 2

2-Hydroxy-3,3-diphenylbutyronitrile 42.3 g (0.201 mol of 2,2-diphenylpropionitrile [sic] were dissolved in 230 ml of THF, and 41.4 g (0.217 mol) of p-toluenesulfonic acid were added. Then 14.09 g (0.217 mol) of KCN in 60 ml of water were added dropwise. The mixture was then heated at 40° C. for 3 hours. The reaction mixture was concentrated to about 30% under reduced pressure, taken up in water and extracted three times with ethyl acetate. The combined organic phases were washed twice with sodium disulfite solution, dried with $MgSO_4$ and concentrated under reduced pressure. The crude product was chromatographed on silica gel with n-heptane/ethyl acetate (20:1). 41.2 g (86%) of 2-hydroxy-3,3-diphenylbutyronitrile were obtained.

$^1$H-NMR [$CDCl_3$], $\delta$=1.9 (s, 3H); 2,7 (d, 1H); 5.1 (d, 1H); 7.2–7.4 (m, 10H).

Example 3

Ethyl 2-Hydroxy-3,3-diphenylbutyrate 1.0 g (4.2 mmol) of 2-hydroxy-3,3-diphenylbutyronitrile was dissolved in 10 ml of ethanol, and 10 ml of conc. HCl [sic] were added. The mixture was refluxed for 24 hours, and then the solvent was stripped off under reduced pressure, and the residue was taken up in water and extracted twice with ethyl acetate. The combined organic phases were washed with 10% strength NaOH, dried with $MgSO_4$ and concentrated under reduced pressure. 0.8 g (67%) of product was obtained.

$^1$H-NMR [$CDCl_3$], $\delta$=0.9 (t, 3H); 1.8 (d, 3H); 3.0 (d, 1H); 3.9 (g, 2H); 5.0 (d, 1H); 7.1–7.4 (m, 10H).

Example 4

2-Hydroxy-3,3-diphenylbutyramide 10.0 g (4.22 [sic] mmol) of 2-hydroxy-3,3-diphenylbutyronitrile were dissolved in 500 ml of methanol (abs.) and, at 5–10° C., HCl was passed in for 3 hours. The mixture was then stirred at 5° C. for 3 hours and at room temperature for 16 hours. Then 200 ml of 6 molar HCl were added and the mixture was evaporated to dryness under reduced pressure. The crude product was recrystallized from an ethyl acetate/heptane mixture. 2.5 g (23%) of 2-hydroxy-3,3-dihenylbutyramide were obtained as a white solid.

Example 5

Ethyl 2-Hydroxy-3,3-diphenylbutyrate 2.15 g (8.4 mmol) of 2-hydroxy-3,3-diphenylbutyramide were dissolved in 15 ml of ethanol, 15 ml of conc. HCl were added and the mixture was refluxed for 40 hours. The solvent was stripped off under reduced pressure, and the residue was taken up in water. The aqueous phase was extracted three times with ethyl acetate, and the combined organic phases were washed twice with 10% strength sodium hydroxide solution. Drying with $MgSO_4$ and stripping off the solvent under reduced pressure resulted in 1.75 g (73%) of ethyl 2-hydroxy-3,3-diphenylbutyrate.

Example 6

2-Hydroxy-3,3-diphenylbutyric Acid 1.75 g (6.2 mmol) of ethyl 2-hydroxy-3,3-diphenylbutyrate were dissolved in 10 ml of THF, and a solution of 0.23 g (9.3 mmol) of LiOH in 6 ml of water was added. The mixture was stirred at room temperature for 16 hours and at 40° C. for 4 hours. The mixture was subsequently concentrated under reduced pressure, taken up in water and washed with ethyl acetate. This was followed by acidification with HCl and extraction three times with ethyl acetate. The combined ethyl acetate phases were dried with $MgSO_4$, and the solvent was stripped off under reduced pressure. The residue was chromatographed on silica gel with $CH_2Cl_2$/MeOH (2:1). 0.80 g (50%) of 2-hydroxy-3,3-diphenylbutyric acid was obtained.

$^1$H-NMR [DMSO-$d_6$], $\delta$=1.75 (s, 3H); 4.85 (s, 1H); 5.5 (s, broad, 1H)); 7.1–7.4 (m, 10H), 12.2 (s, broad, 1H).

Example 7

2-(4,6-Dimethyl-2-pyrimidinyloxy)-3,3-diphenylbutyric Acid 0.29 g (9.5 mmol) of NaH were introduced into DMF and, under nitrogen, 0.80 g (3.15 mmol) of 2-hydroxy-3,3-diphenylbutyric acid in 3 ml of DMF were added. After stirring at room temperature for 30 minutes, 0.45 g (3.15 mmol) of 4,6-dimethyl-1,2-chloropyrimidine in 4 ml of DMF were added, and the mixture was stirred at RT for 16 hours. After the solvent had been stripped off under reduced pressure, the residue was taken up in water, acidified with HCl and extracted twice with ethyl acetate. The combined organic phases were dried with $MgSO_4$, and the solvent was stripped off under reduced pressure. The residue was chromatographed on silica gel with $CH_2Cl_2$/methanol (10:1).

0.37 g (32%) of 2-(4,6-dimethyl-2-pyridinyloxy)-3,3-diphenylbutyric [sic] acid of melting point 225–230° C. was obtained.

$^1$H-NMR [DMSO-$d_6$], $\delta$=1.95 (s, 3H); 2.3 (s, 6H); 5.95 (s, 1H)); 6.8 (s, 1H); 7.0–7.45 (m, 10H).

The compound was fractionated into its two enantiomers by racemate resolution (see Table 2).

Example 8

Methyl 2-Hydroxy-3,3-diphenylbutyrate 15.0 g (63.3 mmol) of 2-hydroxy-3,3-diphenylbutyronitrile were dissolved in 250 ml of absolute methanol and, at 30–50° C., HCl was passed in to saturation. The mixture was then refluxed for 72 hours and subsequently concentrated under reduced pressure, and the residue was taken up in water. The aqueous phase was extracted three times with ethyl acetate; the combined organic phases were dried over $MgSO_4$, the solvent was stripped off under reduced pressure, and the residue was chromatographed on silica gel with n-heptane/ethyl acetate (20:1).

1.2 g (7%) of methyl 2-hydroxy-3,3-diphenylbutyrate were obtained.

$^1$H-NMR [$CDCl_3$], $\delta$=1.8 (s, 3H); 2.95 (d, 1H); 3.45 (s, 3H)); 5.0 (d, 1H); 7.1–7.4 (m, 10H).

Example 9

Methyl 2-(4,6-Dimethoxy-2-pyrimidinyloxy)-3,3-diphenylbutyrate 1.2 g (4.4 mmol) of methyl 2-hydroxy-3,3-diphenylbutyrate were dissolved in 10 ml of absolute DMF and, under nitrogen, 1.2 g (8.8 mmol) of $K_2CO_3$ and 0.97 g (4.4 mmol) of 2-methanesulfonyl-4,6-dimethoxypyrimidine were added. The mixture was stirred at room temperature for 16 hours. It was then evaporated, and the residue was taken up in water and extracted three times with ethyl acetate. The combined organic phases were dried over $MgSO_4$ and concentrated. 1.8 g of crude product were obtained and were reacted further without purification.

$^1$H-NMR [$CDCl_3$], $\delta$=2.0 (s, 3H); 3.25 (s, 3H); 3.9 (s, 6H)); 5.75 (d, 1H); 5.8 (s, 1H); 7.1–7.3 (m, 10H).

Example 10

2-(4,6-Dimethoxy-2-pyrimidinyloxy)-3,3-diphenylbutyric Acid 1.8 g (4.4 mmol) of methyl 2-(4,6-dimethoxy-2-pyrimidinyloxy)-3,3-diphenylbutyrate were dissolved in 25 ml of dioxane, and 26.5 ml (26.5 mmol) of a 1M KOH solution were added, and the mixture was stirred at 90° C. for 6 hours. The mixture was then concentrated, taken up in water and extracted three times with ethyl acetate. The combined organic phases were dried over $MgSO_4$ and evaporated. The residue was recrystallized from ethanol. 1.12 g (65%) of 2-(4,6-dimethoxy-2-pyrimidinyloxy)-3,3-diphenylbutyric acid of melting point 229–234° C. were obtained.

$^1$H-NMR [DMSO-$d_6$], $\delta$=1.9 (s, 3H); 3.85 (s, 6H); 5.85 (s, 1H)); 5.95 (s, 1H); 7.1–7.4 (m, 10H); 12.5 (s, broad, 1H).

Example 11

2,2-Diphenylbutyronitrile 173 ml (0.259 mol) of a 1.5 M solution of LDA in THF were added dropwise to a solution of 50.0 g (0.259 mol) of diphenylacetonitrile in 500 ml of THF (abs.) at −78° C. under argon, and the mixture was then stirred at −30° C. for one hour. Then, at −78° C., 28.23 g (0.259 mol) of ethyl bromide were added. The mixture was allowed to reach room temperature and was stirred for 16 hours. Subsequently, 80 ml of phosphate buffer (pH 7) were added and the mixture was evaporated. The residue was taken up in water and extracted three times with ethyl acetate. The combined organic phases were dried over $MgSO_4$, and the solvent was stripped off under reduced pressure. The crude product was chromatographed on silica gel with n-heptane/acetic acid (20:1). 38.2 g (67%) of 2,2-diphenylbutyronitrile were obtained.

Example 12

2,2-Diphenylbutyraldehyde 21.1 g (95 mmol) of 2,2-diphenylbutyronitrile were dissolved in 100 ml of toluene and, at −78° C. under nitrogen, 95 ml (95 mmol) of a 1 M solution of diisobutylaluminum hydride were added dropwise. The mixture was subsequently stirred at room temperature for 16 hours and then 60 ml of a mixture of saturated ammonium chloride solution and 2 NH$_2$SO$_4$ [sic] in the ratio 2:1 was added, and the mixture was stirred for 30 minutes. The phases were separated and the aqueous phase was extracted three times with ethyl acetate. The combined organic phases were dried over MgSO$_4$ and concentrated under reduced pressure. The crude product was chromatographed on silica gel with dichloromethane. 19.0 g (89%) of 2,2-diphenylbutyraldehyde were obtained as a pale oil.

Example 13

2-Hydroxy-3,3-diphenylvaleronitrile 17.4 g (91.6 mmol) of p-toluenesulfonic acid H$_2$O, and then 5.9 g (91.6 mmol) of KCN in 25 ml of water, were added at 35° C. to a solution of 19.09 g (84.8 mmol) of 2,2-diphenylbutyraldehyde in 97 ml of THF (abs.). The mixture was then stirred at 40° C. for 4 hours and at room temperature for 16 hours. The mixture was evaporated to 1/3 of the volume, water was added, and the phases were separated. The aqueous phase was then extracted three times with ethyl acetate, and the combined organic phases were washed with 10% strength sodium disulfite solution, dried over MgSO$_4$ and concentrated under reduced pressure. The crude product was chromatographed on silica gel with n-heptane/acetic acid (20:1). 19.5 g (92%) of 2-hydroxy-3,3-diphenylvaleronitrile were obtained as a pale oil.

$^1$H-NMR [CDCl$_3$], δ=0.7 (t, 3H); 2.2–2.5 (m, 3H); 5.25 (d, 1H); 7.1–7.4 (m, 10H).

Example 14

2-(4,6-Dimethoxy-2-pyrimidinyloxy)-3,3-diphenylvaleronitrile 7.0 g (27.9 mmol) of 2-hydroxy-3,3-diphenylvaleronitrile were dissolved in 100 ml of DMF (abs.) and, under nitrogen, 7.57 g (55.7 mmol) of potassium carbonate and 6.1 g (27.9 mmol) of 2-methanesulfonyl-4,6-dimethoxypyrimidine were added, and the mixture was stirred at room temperature for 72 hours. The mixture was concentrated under reduced pressure, and the residue was taken up in water and extracted three times with ethyl acetate. The combined organic phases were dried over MgSO$_4$, and the solvent was evaporated off. The crude product was chromatographed on silica gel with n-heptane/ethyl acetate (20:1). 8.8 g (81%) of product were obtained.

$^1$H-NMR [CDCl$_3$], δ=0.8 (t, 3H); 2.45 (dq, 2H); 3.95 (s, 6H), 5.8 (s, 1H); 6.25 (s, 1H); 7.2–7.4 (m, 10H).

Example 15

2-(4,6-Dimethoxy-2-pyrimidinyloxy)-3,3-diphenylvaleric Acid 0.5 g (1.3 mmol) of 2-(4,6-dimethoxy-2-pyrimidinyloxy)-3,3-diphenylvaleronitrile was dissolved in 5 ml of ethanol and, after addition of 5 ml f conc. HCl, the mixture was reflxued for 3 hours. The mixture was then concentrated under reduced pressure, and the residue was taken up in water and extracted twice with ethyl acetate. The combined ethyl acetate phases were dried over MgSO$_4$ and evaporated. The residue was chromatographed by MPLC on reversed phase material with acetonitrile/water as elnent [sic]. 0.17 g (32%) of 2-(4,6-dimethoxy-2-pyrimidinyloxyl-3,3-diphenylvaleric [sic] acid of melting point 78–87° C. was obtained.

$^1$H-NMR [DMSO-d$_6$], δ=0.7 (t, 3H); 2.2–2.55 (m, 2H); 3.85 (s, 6H); 5.9 (s, 2H), 70–74 (m, 10H); 12.7 (s, broad, 1H).

The examples indicated in the following Table 1 can be prepared by the methods described at the outset:

Example 16

Receptor binding data are measured by the binding assay described above for the compounds listed below.

The results are shown in Table 2.

TABLE 2

| Receptor binding data (K$_i$ values) | | |
|---|---|---|
| Compound | ET$_A$ [nM/1] [sic] | ET$_B$ [nM/1] [sic] |
| I-3 | 4 | 325 |
| I-3 Enantiomer I | 0.85 | 73 |
| I-3 Enantiomer I | 450 | >720 |
| I-1 | 25 | 950 |
| I-2 | 3.5 | 290 |
| I-11 | 20 | 1400 |
| I-12 | 4 | 250 |
| I-15 | 4 | 540 |
| I-20 | 5 | 445 |

TABLE 1

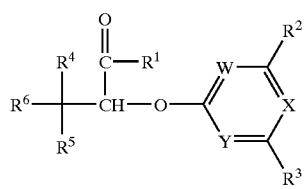

I

| No. | R$^1$ | R$^4$ | R$^5$ | R$^6$ | R$^2$ | X | R$^3$ | Y | W |
|---|---|---|---|---|---|---|---|---|---|
| I-1 | OH | Phenyl | Phenyl | Methyl | OCH$_3$ | CH | OCH$_3$ | N | N |
| I-2 | OH | Phenyl | Phenyl | Methyl | CH$_3$ | CH | OCH$_3$ | N | N |
| I-3 | OH | Phenyl | Phenyl | Methyl | CH$_3$ | CH | CH$_3$ | N | N |

TABLE 1-continued

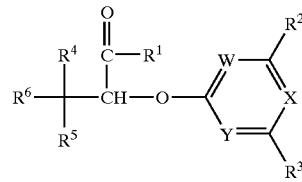

| No. | R¹ | R⁴ | R⁵ | R⁶ | R² | X | R³ | Y | W |
|---|---|---|---|---|---|---|---|---|---|
| I-4 | OH | Phenyl | Phenyl | Methyl | —O—CH$_2$—CH$_2$—C | | OCH$_3$ | N | N |
| I-5 | OH | Phenyl | Phenyl | Methyl | —CH$_2$—CH$_2$—CH$_2$—C | | OCH$_3$ | N | N |
| I-6 | OH | 4-OMe-Phenyl | 4-OMe-Phenyl | Methyl | OCH$_3$ | CH | OCH$_3$ | N | N |
| I-7 | OH | Phenyl | Phenyl | Methyl | Ethyl | CH | Ethyl | N | N |
| I-8 | OH | Phenyl | Phenyl | Methyl | Ethyl | CH | CH$_3$ | N | N |
| I-9 | OH | Phenyl | Phenyl | Ethyl | Ethyl | CH | OCH$_3$ | N | N |
| I-10 | OH | 4-Me-Phenyl | 4-Me-Phenyl | Ethyl | OCH$_3$ | CH | OCH$_3$ | N | N |
| I-11 | OH | Phenyl | Phenyl | Ethyl | OCH$_3$ | CH | OCH$_3$ | N | N |
| I-12 | OH | Phenyl | Phenyl | Ethyl | CH$_3$ | CH | OCH$_3$ | N | N |
| I-13 | OCH$_3$ | Phenyl | Phenyl | Ethyl | CH$_3$ | CH | OCH$_3$ | N | N |
| I-14 | OBenzyl | Phenyl | Phenyl | Ethyl | CH$_3$ | CH | OCH$_3$ | N | N |
| I-15 | OH | Phenyl | Phenyl | Ethyl | CH$_3$ | CH | CH$_3$ | N | N |
| I-16 | OH | Phenyl | Phenyl | Ethyl | —O—CH$_2$—CH$_2$—C | | OCH$_3$ | N | N |
| I-17 | OH | Phenyl | Phenyl | Ethyl | —CH$_2$—CH$_2$—CH$_2$—CH$_2$ | | OCH$_3$ | N | N |
| I-18 | OH | 4-F-Phenyl | 4-F-Phenyl | Ethyl | CH$_3$ | CH | OCH$_3$ | N | N |
| I-19 | OH | 4-F-Phenyl | 4-F-Phenyl | Ethyl | CH$_3$ | CH | CH$_3$ | N | N |
| I-20 | OH | Phenyl | Phenyl | HO—CH$_2$ | CH$_3$ | CH | OCH$_3$ | N | N |
| I-21 | OH | Phenyl | Phenyl | HO—CH$_2$ | CH$_3$ | CH | OCH$_3$ | N | N |
| I-22 | OH | Phenyl | Phenyl | HO—CH$_2$ | CH$_3$ | CH | Ethyl | N | N |
| I-23 | OH | Phenyl | Phenyl | HO—CH$_2$ | —O—CH$_2$—CH$_2$—C | | OCH$_3$ | N | N |
| I-24 | OH | Phenyl | Phenyl | HO—CH$_2$ | —O—CH=CH—C | | OCH$_3$ | N | N |
| I-25 | OH | Phenyl | Phenyl | HO—CH$_2$—CH$_2$ | CH$_3$ | CH | CH$_3$ | N | N |
| I-26 | OH | Phenyl | Phenyl | HO—CH$_2$—CH$_2$ | OCH$_3$ | CH | CH$_3$ | N | N |
| I-27 | OBenzyl | Phenyl | Phenyl | HO—CH$_2$—CH$_2$ | OCH$_3$ | CH | CH$_3$ | N | N |
| I-28 | OH | Phenyl | Phenyl | Benzyl-O—CH$_2$ | CH$_3$ | CH | CH$_3$ | N | N |
| I-29 | OH | Phenyl | Phenyl | 4-Me-Benzyl O—CH$_2$ | CH$_3$ | CH | CH$_3$ | N | N |
| I-30 | OH | Phenyl | Phenyl | 4-Me-Benzyl O—CH$_2$ | CH$_3$ | CH | CH$_3$ | N | N |
| I-31 | OH | Phenyl | Phenyl | HO—CH$_2$—(HO—CH)—CH$_2$ | CH$_3$ | CH | OCH$_3$ | N | N |
| I-32 | OH | Phenyl | Phenyl | HO—CH$_2$—(HO—CH)—CH$_2$ | CH$_3$ | CH | CH$_3$ | N | N |
| I-33 | OH | Phenyl | Phenyl | HO—CH$_2$—(HO—CH)—CH$_2$ | —O—CH$_2$—CH$_2$C | | OCH$_3$ | N | N |
| I-34 | OH | Phenyl | Phenyl | Cl—CH$_2$—CH$_2$ | CH$_3$ | CH | Ethyl | N | N |
| I-35 | OH | Phenyl | Phenyl | Cl—CH$_2$—CH$_2$ | OCH$_3$ | CH | OCH$_3$ | N | N |
| I-36 | OH | Phenyl | Phenyl | Propyl | CH$_3$ | CH | CH$_3$ | N | N |
| I-37 | OH | Phenyl | Phenyl | Propyl | OCH$_3$ | CH | OCH$_3$ | N | N |
| I-38 | OH | Phenyl | Phenyl | Propyl | CH$_3$ | CH | CH$_3$ | N | N |
| I-39 | OH | Phenyl | Phenyl | Propyl | —CH$_2$—CH$_2$—CH$_2$—C | | OCH$_3$ | N | N |
| I-40 | OH | Phenyl | Phenyl | Propyl | —O—CH$_2$—CH$_2$—C | | OCH$_3$ | N | N |
| I-41 | OH | Phenyl | Phenyl | iso-Propyl | CH$_3$ | CH | OCH$_3$ | N | N |
| I-42 | OH | 4-Cl-Phenyl | 4-Cl-Phenyl | Ethyl | CH$_3$ | CH | CH$_3$ | N | N |
| I-43 | OH | 4-Cl-Phenyl | 4-Cl-Phenyl | Ethyl | CH$_3$ | CH | CH$_3$ | N | N |
| I-44 | OBenzyl | Phenyl | Phenyl | Ethyl | CH$_3$ | CH | CH$_3$ | N | N |
| I-45 | OH | Phenyl | Phenyl | 4-Me-Phenyl-CH$_2$—CH$_2$ | CH$_3$ | CH | CH$_3$ | N | N |
| I-46 | OH | Phenyl | Phenyl | 4-OMe-Phenyl-CH$_2$—CH$_2$ | CH$_3$ | CH | CH$_3$ | N | N |
| I-47 | OH | Phenyl | Phenyl | 4-Cl-Phenyl-CH$_2$—CH$_2$ | CH$_3$ | CH | CH$_3$ | N | N |
| I-48 | OH | Phenyl | Phenyl | 4-Me-Phenyl-CH$_2$—CH$_2$—CH$_2$ | CH$_3$ | CH | CH$_3$ | N | N |
| I-49 | OH | Phenyl | Phenyl | 4-OMe-Phenyl-CH$_2$—CH$_2$—CH$_2$ | CH$_3$ | CH | CH$_3$ | N | N |
| I-50 | OH | Phenyl | Phenyl | 4-Cl-Phenyl-CH$_2$—CH$_2$—CH$_2$ | CH$_3$ | CH | CH$_3$ | N | N |
| I-51 | OH | Phenyl | Phenyl | 4-OMe-Phenyl-CH$_2$—CH$_2$—CH$_2$ | CH$_3$ | CH | OCH$_3$ | N | N |
| I-52 | OH | Phenyl | Phenyl | 4-Me-Phenyl-CH$_2$—CH$_2$—CH$_2$ | CH$_3$ | CH | OCH$_3$ | N | N |
| I-53 | OH | Phenyl | Phenyl | 4-Cl-Phenyl-CH$_2$—CH$_2$—CH$_2$ | CH$_3$ | CH | OCH$_3$ | N | N |
| I-54 | OH | Phenyl | Phenyl | 4-OMe-Phenyl-CH$_2$—CH$_2$—CH$_2$ | —O—CH$_2$—CH$_2$—C | | CH$_3$ | N | N |

TABLE 1-continued

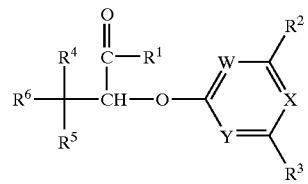

I

| No. | R¹ | R⁴ | R⁵ | R⁶ | R² | X | R³ | Y | W |
|---|---|---|---|---|---|---|---|---|---|
| I-55 | OH | Phenyl | Phenyl | 4-Me-Phenyl-CH₂—CH₂—CH₂ | —O—CH₂—CH₂—C | CH₃ | N | N |
| I-56 | OH | Phenyl | Phenyl | 4-Cl-Phenyl-CH₂—CH₂—CH₂ | —O—CH₂—CH₂—C | OCH₃ | N | N |
| I-57 | OH | 4-F-Phenyl | 4-F-Phenyl | 4-OMe-Phenyl-CH₂—CH₂—CH₂ | —O—CH₂—CH₂—C | OCH₃ | N | N |
| I-58 | OH | 4-F-Phenyl | 4-F-Phenyl | 4-OMe-Phenyl-CH₂—CH₂—CH₂ | —O—CH₂—CH₂—C | OCH₃ | N | N |
| I-59 | OH | 4-F-Phenyl | 4-F-Phenyl | 4-Cl-Phenyl-CH₂—CH₂—CH₂ | —O—CH₂—CH₂—C | OCH₃ | N | N |
| I-60 | OH | 4-F-Phenyl | 4-F-Phenyl | 4-OMe-Phenyl-CH₂—CH₂—CH₂ | CH₃ | CH | CH₃ | N | N |
| I-61 | OH | 4-F-Phenyl | 4-F-Phenyl | 4-Me-Phenyl-CH₂—CH₂—CH₂ | CH₃ | CH | CH₃ | N | N |
| I-62 | OH | 4-F-Phenyl | 4-F-Phenyl | 4-Cl-Phenyl-CH₂—CH₂—CH₂ | CH₃ | CH | CH₃ | N | N |
| I-63 | OH | 4-Me-Phenyl | 4-Me-Phenyl | 4-OMe-Phenyl-CH₂—CH₂—CH₂ | CH₃ | CH | CH₃ | N | N |
| I-64 | OH | 4-Me-Phenyl | 4-Me-Phenyl | 4-Me-Phenyl-CH₂—CH₂—CH₂ | CH₃ | CH | CH₃ | N | N |
| I-65 | OH | 4-Me-Phenyl | 4-Me-Phenyl | 4-Cl-Phenyl-CH₂—CH₂—CH₂ | CH₃ | CH | CH₃ | N | N |
| I-66 | OH | Phenyl | Phenyl | HOOC—CH₂ | CH₃ | CH | CH₃ | N | N |
| I-67 | OH | Phenyl | Phenyl | HOOC—CH₂ | CH₃ | CH | CH₃ | N | N |
| I-68 | OH | Phenyl | Phenyl | HOOC—CH₂ | —O—CH₂—CH₂—C | OCH₃ | N | N |
| I-69 | OH | Phenyl | Phenyl | HOOC—CH₂ | —CH₂—CH₂—CH₂—C | OCH₃ | N | N |
| I-70 | OH | Phenyl | Phenyl | HOOC—CH₂ | Ethyl | CH | CH₃ | N | N |
| I-71 | OH | Phenyl | Phenyl | HOOC—CH₂ | Ethyl | CH | Ethyl | N | N |
| I-72 | OH | Phenyl | Phenyl | HOOC—CH₂—CH₂ | OCH₃ | CH | CH₃ | N | N |
| I-73 | OH | Phenyl | Phenyl | HOOC—CH₂—CH₂ | CH₃ | CH | CH₃ | N | N |
| I-74 | OH | Phenyl | Phenyl | HOOC—CH₂—CH₂ | Ethyl | CH | CH₃ | N | N |
| I-75 | OH | Phenyl | Phenyl | HOOC—CH₂—CH₂ | —O—CH₂—CH₂—C | OCH₃ | N | N |
| I-76 | OH | 4-OMe-Phenyl | 4-OMe-Phenyl | Methyl | OCH₃ | CH | OCH₃ | N | N |
| I-77 | OH | 4-OMe-Phenyl | 4-OMe-Phenyl | Methyl | CH₃ | CH | OCH₃ | N | N |
| I-78 | OH | 4-OMe-Phenyl | 4-OMe-Phenyl | Methyl | CH₃ | CH | CH₃ | N | N |
| I-79 | OH | 4-OMe-Phenyl | 4-OMe-Phenyl | Methyl | CH₃ | CH | Ethyl | N | N |
| I-80 | OH | 4-OMe-Phenyl | 4-OMe-Phenyl | Methyl | —O—CH₂—CH₂—C | OCH₃ | N | N |
| I-81 | OH | 4-OMe-Phenyl | 4-OMe-Phenyl | Ethyl | OCH₃ | CH | OCH₃ | N | N |
| I-82 | OH | 4-OMe-Phenyl | 4-OMe-Phenyl | Ethyl | CH₃ | CH | OCH₃ | N | N |
| I-83 | OH | 4-OMe-Phenyl | 4-OMe-Phenyl | Ethyl | CH₃ | CH | CH₃ | N | N |
| I-84 | OH | 4-OMe-Phenyl | 4-OMe-Phenyl | 4-Me-Benzyl-O—CH₂ | CH₃ | CH | OCH₃ | N | N |
| I-85 | OH | 4-OMe-Phenyl | 4-OMe-Phenyl | 4-Me-Benzyl-O—CH₂ | CH₃ | CH | CH₃ | N | N |
| I-86 | OH | 4-OMe-Phenyl | 4-OMe-Phenyl | 4-Me-Benzyl-O—CH₂ | CH₃ | CH | Ethyl | N | N |
| I-87 | OH | 4-OMe-Phenyl | 4-OMe-Phenyl | 4-OMe-Benzyl-O—CH₂ | OCH₃ | CH | CH₃ | N | N |
| I-88 | OH | 4-OMe-Phenyl | 4-OMe-Phenyl | 4-OMe-Benzyl-O—CH₂ | CH₃ | CH | CH₃ | N | N |
| I-89 | OH | 4-OMe-Phenyl | 4-OMe-Phenyl | 4-OMe-Benzyl-O—CH₂ | —O—CH₂—CH₂—C | OCH₃ | N | N |
| I-90 | OH | 4-OMe-Phenyl | 4-OMe-Phenyl | 4-OMe-Phenyl-CH₂—CH₂—CH₂ | CH₃ | CH | CH₃ | N | N |
| I-91 | OH | 4-OMe-Phenyl | 4-OMe-Phenyl | 4-OMe-Phenyl-CH₂—CH₂—CH₂ | CH₃ | CH | CH₃ | N | N |
| I-92 | OH | 4-OMe-Phenyl | 4-OMe-Phenyl | 4-OMe-Phenyl-CH₂—CH₂—CH₂ | —O—CH₂—CH₂—C | OCH₃ | N | N |
| I-93 | OH | Phenyl | Phenyl | 4-OMe-Phenyl-CH₂—CH₂—CH₂—CH₂ | CH₃ | CH | OCH₃ | N | N |
| I-94 | OH | Phenyl | Phenyl | 4-OMe-Phenyl-CH₂—CH₂—CH₂—CH₂ | CH₃ | CH | CH₃ | N | N |
| I-95 | OH | Phenyl | Phenyl | 4-OMe-Phenyl-CH₂—CH₂—CH₂—CH₂ | —O—CH₂—CH₂—C | OCH₃ | N | N |
| I-96 | OH | Phenyl | Phenyl | 4-OMe-Phenyl-CH₂—CH₂—CH₂—CH₂ | CH₃ | CH | Ethyl | N | N |

TABLE 1-continued

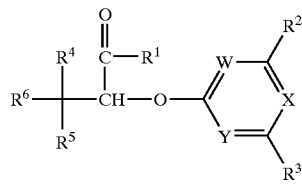

| No. | R¹ | R⁴ | R⁵ | R⁶ | R² | X | R³ | Y | W |
|---|---|---|---|---|---|---|---|---|---|
| I-97 | OH | Phenyl | Phenyl | 4-Me-Phenyl-CH$_2$—CH$_2$—CH$_2$—CH$_2$ | CH$_3$ | CH | OCH$_3$ | N | N |
| I-98 | OH | Phenyl | Phenyl | 4-Me-Phenyl-CH$_2$—CH$_2$—CH$_2$—CH$_2$ | CH$_3$ | CH | CH$_3$ | N | N |
| I-99 | OH | Phenyl | Phenyl | 4-Me-Phenyl-CH$_2$—CH$_2$—CH$_2$—CH$_2$ | —O—CH$_2$—CH$_2$—C | | OCH$_3$ | N | N |
| I-100 | OH | Phenyl | Phenyl | 4-Me-Phenyl-CH$_2$—CH$_2$—CH$_2$—CH$_2$ | Ethyl | CH | CH$_3$ | N | N |
| I-101 | OH | Phenyl | Phenyl | Methyl | CH$_3$ | CH | SCH$_3$ | N | N |
| I-102 | OH | Phenyl | Phenyl | Methyl | N(CH$_3$)$_2$ | CH | N(CH$_3$)$_2$ | N | N |
| I-103 | OH | Phenyl | Phenyl | Methyl | OCH$_3$ | CH | SCH$_3$ | N | N |
| I-104 | OH | Phenyl | Phenyl | Ethyl | CH$_3$ | CH | SCH$_3$ | N | N |
| I-105 | OH | Phenyl | Phenyl | Ethyl | N(CH$_3$)$_2$ | CH | N(CH$_3$)$_2$ | N | N |
| I-106 | OH | Phenyl | Phenyl | iso-Propyl | CH$_3$ | CH | SCH$_3$ | N | N |
| I-107 | OH | Phenyl | Phenyl | 4-OMe-Phenyl-CH$_2$—CH$_2$—CH$_2$ | CH$_3$ | CH | SCH$_3$ | N | N |
| I-108 | OH | Phenyl | Phenyl | 4-Me-Phenyl-CH$_2$—CH$_2$—CH$_2$ | CH$_3$ | CH | SCH$_3$ | N | N |
| I-109 | OH | Phenyl | Phenyl | 4-SMe-Phenyl-CH$_2$—CH$_2$—CH$_2$ | CH$_3$ | CH | CH$_3$ | N | N |
| I-110 | OH | Phenyl | Phenyl | 4-SMe-Phenyl-CH$_2$—CH$_2$—CH$_2$ | OCH$_3$ | CH | CH$_3$ | N | N |
| I-111 | OH | Phenyl | Phenyl | 4-SMe-Phenyl-CH$_2$—CH$_2$—CH$_2$ | O—CH$_2$—CH$_2$—C— | | OCH$_3$ | N | N |
| I-112 | OH | Phenyl | Phenyl | 4-SMe-Phenyl-CH$_2$—CH$_2$—CH$_2$ | CH$_2$—CH$_2$—CH$_2$—C— | | OCH$_3$ | N | N |
| I-113 | OH | 4-F-Phenyl | 4-F-Phenyl | 4-SMe-Phenyl-CH$_2$—CH$_2$—CH$_2$— | CH$_3$ | CH | CH$_3$ | N | N |
| I-114 | OH | 4-F-Phenyl | 4-F-Phenyl | 4-SMe-Phenyl-CH$_2$—CH$_2$—CH$_2$ | CH$_3$ | CH | OCH$_3$ | N | N |
| I-115 | OH | 4-Me-Phenyl | 4-Me-Phenyl | 4-SMe-Phenyl-CH$_2$—CH$_2$—CH$_2$ | OCH$_3$ | CH | CH$_3$ | N | N |
| I-116 | OH | 4-Me-Phenyl | 4-Me-Phenyl | 4-SMe-Phenyl-CH$_2$—CH$_2$—CH$_2$ | CH$_3$ | CH | CH$_3$ | N | N |
| I-117 | OH | 4-Me-Phenyl | 4-Me-Phenyl | 4-SMe-Phenyl-CH$_2$—CH$_2$—CH$_2$ | O—CH$_2$—CH$_2$—C— | | OCH$_3$ | N | N |
| I-118 | OH | Phenyl | Phenyl | 4-Ethyl-Phenyl-CH$_2$—CH$_2$—CH$_2$ | CH$_3$ | CH | CH$_3$ | N | N |
| I-119 | OH | Phenyl | Phenyl | HO—CH$_2$— | CH$_3$ | CH | SCH$_3$ | N | N |
| I-120 | OH | Phenyl | Phenyl | HO—CH$_2$—CH$_2$ | CH$_3$ | CH | SCH$_3$ | N | N |
| I-121 | OH | Phenyl | Phenyl | HOOC—CH$_2$—CH$_2$ | CH$_3$ | CH | SCH$_3$ | N | N |
| I-122 | OH | Phenyl | Phenyl | Methyl | OCH$_3$ | N | OCH$_3$ | N | N |
| I-123 | OH | Phenyl | Phenyl | Methyl | CH$_3$ | N | OCH$_3$ | N | N |
| I-124 | OH | Phenyl | Phenyl | Methyl | CH$_3$ | N | CH$_3$ | N | N |
| I-125 | OH | Phenyl | Phenyl | Methyl | Ethyl | N | Ethyl | N | N |
| I-126 | OH | Phenyl | Phenyl | Methyl | Ethyl | N | CH$_3$ | N | N |
| I-127 | OH | Phenyl | Phenyl | Ethyl | Ethyl | N | OCH$_3$ | N | N |
| I-128 | OH | Phenyl | Phenyl | Ethyl | OCH$_3$ | N | OCH$_3$ | N | N |
| I-129 | OH | Phenyl | Phenyl | Ethyl | CH$_3$ | N | OCH$_3$ | N | N |
| I-130 | OH | Phenyl | Phenyl | Ethyl | CH$_3$ | N | CH$_3$ | N | N |
| I-131 | OH | Phenyl | Phenyl | HO—CH$_2$ | CH$_3$ | N | OCH$_3$ | N | N |
| I-132 | OH | Phenyl | Phenyl | HO—CH$_2$ | CH$_3$ | N | CH$_3$ | N | N |
| I-133 | OH | Phenyl | Phenyl | HO—CH$_2$ | CH$_3$ | N | Ethyl | N | N |
| I-134 | OH | Phenyl | Phenyl | HO—CH$_2$—CH$_2$ | CH$_3$ | N | CH$_3$ | N | N |
| I-135 | OH | Phenyl | Phenyl | Benzyl-O—CH$_2$ | CH$_3$ | N | CH$_3$ | N | N |
| I-136 | OH | Phenyl | Phenyl | 4-Me-Benzyl-O—CH$_2$ | CH$_3$ | N | CH$_3$ | N | N |
| I-137 | OH | Phenyl | Phenyl | 4-OMe-Benzyl-O—CH$_2$ | CH$_3$ | N | CH$_3$ | N | N |
| I-138 | OH | Phenyl | Phenyl | HO—CH$_2$—(HO—CH)—CH$_2$ | CH$_3$ | N | OCH$_3$ | N | N |
| I-139 | OH | Phenyl | Phenyl | Propyl | CH$_3$ | N | OCH$_3$ | N | N |
| I-140 | OH | Phenyl | Phenyl | Propyl | CH$_3$ | N | CH$_3$ | N | N |
| I-141 | OH | Phenyl | Phenyl | Propyl | OCH$_3$ | N | OCH$_3$ | N | N |

TABLE 1-continued

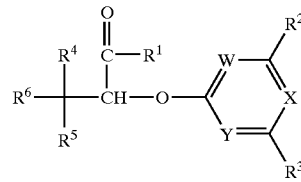

I

| No. | R¹ | R⁴ | R⁵ | R⁶ | R² | X | R³ | Y | W |
|---|---|---|---|---|---|---|---|---|---|
| I-142 | OH | Phenyl | Phenyl | iso-Propyl | $CH_3$ | N | $CH_3$ | N | N |
| I-143 | OH | 4-OMe-Phenyl | 4-OMe-Phenyl | Methyl | $OCH_3$ | N | $OCH_3$ | N | N |
| I-144 | OH | 4-OMe-Phenyl | 4-OMe-Phenyl | Ethyl | $CH_3$ | N | $OCH_3$ | N | N |
| I-145 | OH | 4-OMe-Phenyl | 4-OMe-Phenyl | Ethyl | $CH_3$ | N | $CH_3$ | N | N |
| I-146 | OH | 4-OMe-Phenyl | 4-OMe-Phenyl | Methyl | $CH_3$ | N | $CH_3$ | N | N |
| I-147 | OH | 4-OMe-Phenyl | 4-OMe-Phenyl | 4-OMe-Phenyl-$CH_2$—$CH_2$—$CH_2$ | $CH_3$ | N | $CH_3$ | N | N |
| I-148 | OH | 4-OMe-Phenyl | 4-OMe-Phenyl | 4-OMe-Phenyl-$CH_2$—$CH_2$—$CH_2$ | $CH_3$ | N | $OCH_3$ | N | N |
| I-149 | OH | 4-Me-Phenyl | 4-Me-Phenyl | Ethyl | $CH_3$ | N | $OCH_3$ | N | N |
| I-150 | OH | 4-Me-Phenyl | 4-Me-Phenyl | Methyl | $CH_3$ | N | $CH_3$ | N | N |
| I-151 | OH | 4-Me-Phenyl | 4-Me-Phenyl | 4-Me-Phenyl-$CH_2$—$CH_2$—$CH_2$ | $CH_3$ | N | $CH_3$ | N | N |
| I-152 | OH | 4-Me-Phenyl | 4-Me-Phenyl | 4-Me-Phenyl-$CH_2$—$CH_2$—$CH_2$ | $CH_3$ | N | $CH_3$ | N | N |
| I-153 | OH | Phenyl | Phenyl | 4-OMe-Phenyl-$CH_2$—$CH_2$—$CH_2$ | $CH_3$ | N | $CH_3$ | N | N |
| I-154 | OH | Phenyl | Phenyl | 4-Me-Phenyl-$CH_2$—$CH_2$—$CH_2$ | $CH_3$ | N | $CH_3$ | N | N |
| I-155 | OH | Phenyl | Phenyl | 4-SMe-Phenyl-$CH_2$—$CH_2$—$CH_2$ | $CH_3$ | N | $CH_3$ | N | N |
| I-156 | OH | Phenyl | Phenyl | 4-SMe-Phenyl-$CH_2$—$CH_2$—$CH_2$ | $OCH_3$ | N | $CH_3$ | N | N |
| I-157 | OH | Phenyl | Phenyl | HOOC—$CH_2$ | $CH_3$ | N | $CH_3$ | N | N |
| I-158 | OH | Phenyl | Phenyl | Methyl | $CH_3$ | N | $SCH_3$ | N | N |
| I-159 | OH | Phenyl | Phenyl | Methyl | $N(CH_3)_2$ | N | $N(CH_3)_2$ | N | N |
| I-160 | OH | Phenyl | Phenyl | Ethyl | $CH_3$ | N | $SCH_3$ | N | N |
| I-161 | OH | Phenyl | Phenyl | Methyl | $OCH_3$ | N | $OCH_3$ | CH | N |
| I-162 | OH | Phenyl | Phenyl | Methyl | $OCH_3$ | N | $CH_3$ | CH | N |
| I-163 | OH | Phenyl | Phenyl | Methyl | $CH_3$ | N | $OCH_3$ | CH | N |
| I-164 | OH | Phenyl | Phenyl | Methyl | $CH_3$ | N | $CH_3$ | CH | N |
| I-165 | OH | Phenyl | Phenyl | Methyl | $CH_3$ | N | Ethyl | CH | N |
| I-166 | OH | Phenyl | Phenyl | Methyl | Ethyl | N | Ethyl | CH | N |
| I-167 | OH | Phenyl | Phenyl | Methyl | Ethyl | N | $CH_3$ | CH | N |
| I-168 | OH | Phenyl | Phenyl | Methyl | $OCH_3$ | N | $SCH_3$ | CH | N |
| I-169 | OH | Phenyl | Phenyl | Methyl | $OCH_3$ | N | $CF_3$ | CH | N |
| I-170 | OH | Phenyl | Phenyl | Ethyl | $OCH_3$ | N | $OCH_3$ | CH | N |
| I-171 | OH | Phenyl | Phenyl | Ethyl | $CH_3$ | N | $CH_3$ | CH | N |
| I-172 | OH | Phenyl | Phenyl | Ethyl | $OCH_3$ | N | $CH_3$ | CH | N |
| I-173 | OH | Phenyl | Phenyl | Ethyl | $CH_3$ | N | $OCH_3$ | CH | N |
| I-174 | OH | Phenyl | Phenyl | Ethyl | $CH_3$ | N | Ethyl | CH | N |
| I-175 | OH | Phenyl | Phenyl | Ethyl | Ethyl | N | Ethyl | CH | N |
| I-176 | OH | Phenyl | Phenyl | Ethyl | Ethyl | N | $CH_3$ | CH | N |
| I-177 | OH | Phenyl | Phenyl | Ethyl | $OCH_3$ | N | $SCH_3$ | CH | N |
| I-178 | OH | Phenyl | Phenyl | Ethyl | $OCH_3$ | N | $CF_3$ | CH | N |
| I-179 | OH | Phenyl | Phenyl | Propyl | $CH_3$ | N | $CH_3$ | CH | N |
| I-180 | OH | Phenyl | Phenyl | Propyl | $OCH_3$ | N | $CH_3$ | CH | N |
| I-181 | OH | Phenyl | Phenyl | Propyl | $CH_3$ | N | $OCH_3$ | CH | N |
| I-182 | OH | Phenyl | Phenyl | HO—$CH_2$ | $CH_3$ | N | $CH_3$ | CH | N |
| I-183 | OH | Phenyl | Phenyl | HO—$CH_2$ | $OCH_3$ | N | $CH_3$ | CH | N |
| I-184 | OH | Phenyl | Phenyl | HO—$CH_2$ | $CH_3$ | N | $OCH_3$ | CH | N |
| I-185 | OH | Phenyl | Phenyl | HO—$CH_2$(OH—CH)—$CH_2$ | $CH_3$ | N | $CH_3$ | CH | N |
| I-186 | OH | Phenyl | Phenyl | HO—$CH_2$(OH—CH)—$CH_2$ | $CH_3$ | N | $OCH_3$ | CH | N |
| I-187 | OH | Phenyl | Phenyl | HO—$CH_2$(OH—CH)—$CH_2$ | $OCH_3$ | N | $CH_3$ | CH | N |
| I-188 | OH | Phenyl | Phenyl | 4-OMe-Phenyl-$CH_2$—$CH_2$—$CH_2$ | $CH_3$ | N | $CH_3$ | CH | N |

TABLE 1-continued

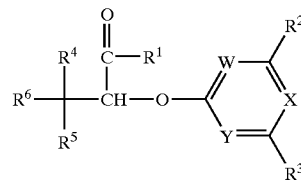

I

| No. | R¹ | R⁴ | R⁵ | R⁶ | R² | X | R³ | Y | W |
|---|---|---|---|---|---|---|---|---|---|
| I-189 | OH | Phenyl | Phenyl | 4-OMe-Phenyl-CH$_2$—CH$_2$—CH$_2$ | OCH$_3$ | N | CH$_3$ | CH | N |
| I-190 | OH | Phenyl | Phenyl | 4-OMe-Phenyl-CH$_2$—CH$_2$—CH$_2$ | CH$_3$ | N | OCH$_3$ | CH | N |
| I-191 | OH | Phenyl | Phenyl | 4-OMe-Phenyl-CH$_2$—CH$_2$—CH$_2$ | Ethyl | N | CH$_3$ | CH | N |
| I-192 | OH | Phenyl | Phenyl | 4-SMe-Phenyl-CH$_2$—CH$_2$—CH$_2$ | OCH$_3$ | N | CH$_3$ | CH | N |
| I-193 | OH | Phenyl | Phenyl | 4-SMe-Phenyl-CH$_2$—CH$_2$—CH$_2$ | CH$_3$ | N | OCH$_3$ | CH | N |
| I-194 | OH | Phenyl | Phenyl | 4-SMe-Phenyl-CH$_2$—CH$_2$—CH$_2$ | OCH$_3$ | N | CH$_3$ | CH | N |
| I-195 | OH | Phenyl | Phenyl | 4-SMe-Phenyl-CH$_2$—CH$_2$—CH$_2$ | Ethyl | N | Ethyl | CH | N |
| I-196 | OH | Phenyl | Phenyl | 4-SMe-Phenyl-CH$_2$—CH$_2$—CH$_2$ | CH$_3$ | N | Ethyl | CH | N |
| I-197 | OH | Phenyl | Phenyl | HOOC—CH$_2$ | CH$_3$ | N | CH$_3$ | CH | N |
| I-198 | OH | Phenyl | Phenyl | HOOC—CH$_2$ | CH$_3$ | N | Ethyl | CH | N |
| I-199 | OH | Phenyl | Phenyl | HOOC—CH$_2$ | CH$_3$ | N | OCH$_3$ | CH | N |
| I-200 | OH | Phenyl | Phenyl | HOOC—CH$_2$ | OCH$_3$ | N | CH$_3$ | CH | N |
| I-201 | OH | 4-F-Phenyl | 4-F-Phenyl | Methyl | CH$_3$ | N | CH$_3$ | CH | N |
| I-202 | OH | 4-OMe-Phenyl | 4-OMe-Phenyl | Methyl | CH$_3$ | N | CH$_3$ | CH | N |
| I-203 | OH | 4-Me-Phenyl | 4-MePhenyl | Methyl | CH$_3$ | N | CH$_3$ | CH | N |
| I-204 | OH | 4-Me-Phenyl | 4-MePhenyl | Ethyl | CH$_3$ | N | CH$_3$ | CH | N |
| I-205 | OH | 4-Me-Phenyl | 4-Me-Phenyl | Ethyl | CH$_3$ | N | OCH$_3$ | CH | N |
| I-206 | OH | 4-Me-Phenyl | 4-Me-Phenyl | Ethyl | OCH$_3$ | N | CH$_3$ | CH | N |
| I-207 | OH | 4-Me-Phenyl | 4-Me-Phenyl | Ethyl | Ethyl | N | CF$_3$ | CH | N |
| I-208 | OH | 4-Me-Phenyl | 4-Me-Phenyl | HOOC—CH$_2$—CH$_2$ | CH$_3$ | N | CH$_3$ | CH | N |
| I-209 | OH | 4-Me-Phenyl | 4-Me-Phenyl | HOOC—CH$_2$—CH$_2$ | OCH$_3$ | N | CH$_3$ | CH | N |
| I-210 | OH | 4-Me-Phenyl | 4-Me-Phenyl | HOOC—CH$_2$—CH$_2$ | Ethyl | N | CH$_3$ | CH | N |
| I-211 | OH | Phenyl | Phenyl | HOOC—CH$_2$—CH$_2$ | CH$_3$ | N | CH$_3$ | CH | N |
| I-212 | OH | Phenyl | Phenyl | HOOC—CH$_2$—CH$_2$ | OCH$_3$ | N | CH$_3$ | CH | N |
| I-213 | OH | Phenyl | Phenyl | HOOC—CH$_2$—CH$_2$ | Ethyl | N | CH$_3$ | CH | N |
| I-214 | OH | Phenyl | Phenyl | HOOC—CH$_2$—CH$_2$ | Ethyl | N | CF$_3$ | CH | N |
| I-215 | OH | Phenyl | Phenyl | HOOC—CH$_2$—CH$_2$ | CH$_3$ | N | OCH$_3$ | CH | N |
| I-216 | OH | Phenyl | Phenyl | HOOC—CH$_2$—CH$_2$ | CH$_3$ | N | Ethyl | CH | N |
| I-217 | OH | Phenyl | Phenyl | HOOC—CH$_2$—CH$_2$ | CF$_3$ | N | Ethyl | CH | N |
| I-218 | OH | Phenyl | Phenyl | HO—CH$_2$—(HO—CH)—CH$_2$ | CF$_3$ | N | Ethyl | CH | N |
| I-219 | OH | Phenyl | Phenyl | HO—CH$_2$—(HO—CH)—CH$_2$ | CH$_3$ | N | Ethyl | CH | N |
| I-220 | OH | Phenyl | Phenyl | HO—CH$_2$—(HO—CH)—CH$_2$ | Ethyl | N | CH$_3$ | CH | N |
| I-221 | OH | Phenyl | Phenyl | (HO—CH$_2$)$_2$CH—CH$_2$ | CH$_3$ | N | CH$_3$ | CH | N |
| I-222 | OH | Phenyl | Phenyl | (HO—CH$_2$)$_2$CH—CH$_2$ | OCH$_3$ | N | CH$_3$ | CH | N |
| I-223 | OH | Phenyl | Phenyl | (HO—CH$_2$)$_2$CH—CH$_2$ | CH$_3$ | N | OCH$_3$ | CH | N |
| I-224 | OH | Phenyl | Phenyl | (HO—CH$_2$)$_2$CH—CH$_2$ | CH$_3$ | N | Ethyl | CH | N |
| I-225 | OH | Phenyl | Phenyl | Methyl | CH=CH—CH=CH—C | | CH$_3$ | CH | N |
| I-226 | OH | Phenyl | Phenyl | Methyl | CH=CH—CH=CH—C | | H | CH | N |
| I-227 | OH | Phenyl | Phenyl | Methyl | CH$_3$ | CH | CH$_3$ | CH | N |
| I-228 | OH | Phenyl | Phenyl | Methyl | CH$_3$ | CH | OCH$_3$ | CH | N |
| I-229 | OH | Phenyl | Phenyl | Methyl | CH$_3$ | CH | Ethyl | CH | N |
| I-230 | OH | Phenyl | Phenyl | Methyl | Ethyl | CH | CH$_3$ | CH | N |
| I-231 | OH | Phenyl | Phenyl | Ethyl | CH=CH—CH=CH—C | | CH$_3$ | CH | N |
| I-232 | OH | Phenyl | Phenyl | Ethyl | CH=CH—CH=CH—C | | H | CH | N |
| I-233 | OH | Phenyl | Phenyl | Propyl | CH=CH—CH=CH—C | | CH$_3$ | CH | N |
| I-234 | OH | Phenyl | Phenyl | Ethyl | CH$_2$—CH$_2$—CH$_2$—C | | CH$_3$ | CH | N |
| I-235 | OH | Phenyl | Phenyl | Methyl | CH$_2$—CH$_2$—CH$_2$—C | | CH$_3$ | CH | N |
| I-236 | OH | Phenyl | Phenyl | Propyl | CH$_2$—CH$_2$—CH$_2$—C | | CH$_3$ | CH | N |
| I-237 | OH | Phenyl | Phenyl | Ethyl | CH$_3$ | CH | Ethyl | CH | N |
| I-238 | OH | Phenyl | Phenyl | Ethyl | CH$_3$ | CH | CH$_3$ | CH | N |
| I-239 | OH | Phenyl | Phenyl | Ethyl | Ethyl | CH | CH$_3$ | CH | N |
| I-240 | OH | Phenyl | Phenyl | Ethyl | CH$_3$ | CH | OCH$_3$ | CH | N |
| I-241 | OH | Phenyl | Phenyl | Methyl | OCH$_3$ | XH | CH$_3$ | CH | N |
| I-242 | OH | Phenyl | Phenyl | Methyl | O—CH$_2$—CH$_2$—C | | H | CH | N |
| I-243 | OH | Phenyl | Phenyl | Methyl | O—CH$_2$—CH$_2$—C | | CH$_3$ | CH | N |

TABLE 1-continued

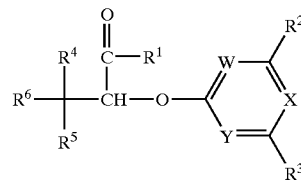

| No. | R¹ | R⁴ | R⁵ | R⁶ | R² | X | R³ | Y | W |
|---|---|---|---|---|---|---|---|---|---|
| I-244 | OH | Phenyl | Phenyl | Ethyl | OCH₃ | CH | CH₃ | CH | N |
| I-245 | OH | Phenyl | Phenyl | Ethyl | O—CH₂—CH₂—C | | H | CH | N |
| I-246 | OH | Phenyl | Phenyl | Ethyl | O—CH₂—CH₂—C | | CH₃ | CH | N |
| I-247 | OH | Phenyl | Phenyl | Ethyl | O—CH₂—O—C | | H | CH | N |
| I-248 | OH | Phenyl | Phenyl | Ethyl | O—CH₂—O—C | | CH₃ | CH | N |
| I-249 | OH | Phenyl | Phenyl | Ethyl | CH₃ | CH | CH=CH—CH=CH—C | | N |
| I-250 | OH | Phenyl | Phenyl | Ethyl | OCH₃ | CH | CH=CH—CH=CH—C | | N |
| I-251 | OH | Phenyl | Phenyl | Methyl | CH₃ | CH | CH=CH—CH=CH—C | | N |
| I-252 | OH | Phenyl | Phenyl | Methyl | OCH₃ | CH | CH=CH—CH=CH—C | | N |
| I-253 | OH | Phenyl | Phenyl | Methyl | CH₃ | CH | O—CH₂—O—C | | N |
| I-254 | OH | Phenyl | Phenyl | Methyl | OCH₃ | CH | O—CH₂—O—C | | N |
| I-255 | OH | Phenyl | Phenyl | Ethyl | CH₃ | CH | O—CH₂—O—C | | N |
| I-256 | OH | Phenyl | Phenyl | Ethyl | OCH₃ | CH | O—CH₂—O—C | | N |
| I-257 | OH | Phenyl | Phenyl | Ethyl | CH₃ | CH | CH₂—CH₂—O—C | | N |
| I-258 | OH | Phenyl | Phenyl | Ethyl | OCH₃ | CH | CH₂—CH₂—O—C | | N |
| I-259 | OH | Phenyl | Phenyl | Methyl | CH₃ | CH | CH₂—CH₂—O—C | | N |
| I-260 | OH | Phenyl | Phenyl | Methyl | OCH₃ | CH | CH₂—CH₂—O—C | | N |
| I-261 | OH | Phenyl | Phenyl | Methyl | CH₃ | CH | N=CH—NH—C | | N |
| I-262 | OH | Phenyl | Phenyl | Methyl | OCH₃ | CH | N=CH—NH—C | | N |
| I-263 | OH | Phenyl | Phenyl | Ethyl | CH₃ | CH | N=CH—NH—C | | N |
| I-264 | OH | Phenyl | Phenyl | Ethyl | OCH₃ | CH | N=CH—NH—C | | N |
| I-265 | OH | Phenyl | Phenyl | Ethyl | CH₃ | CH | CH=CH—NH—C | | N |
| I-266 | OH | Phenyl | Phenyl | Ethyl | OCH₃ | CH | CH=CH—NH—C | | N |
| I-267 | OH | Phenyl | Phenyl | HO—CH₂ | CH₃ | CH | CH=CH—NH—C | | N |
| I-268 | OH | Phenyl | Phenyl | HO—CH₂ | OCH₃ | CH | CH=CH—NH—C | | N |
| I-269 | OH | Phenyl | Phenyl | HO—CH₂—CH₂ | CH₃ | CH | CH=CH—NH—C | | N |
| I-270 | OH | Phenyl | Phenyl | HO—CH₂—CH₂ | OCH₃ | CH | CH=CH—NH—C | | N |
| I-271 | OH | Phenyl | Phenyl | Methyl | CH₃ | CH | CH=CH—NH—C | | N |
| I-272 | OH | Phenyl | Phenyl | Methyl | OCH₃ | CH | CH=CH—NH—C | | N |
| I-273 | OH | Phenyl | Phenyl | Methyl | CH₃ | N | CH=CH—NH—C | | N |
| I-274 | OH | Phenyl | Phenyl | Methyl | OCH₃ | N | CH=CH—NH—C | | N |
| I-275 | OH | Phenyl | Phenyl | Ethyl | CH₃ | N | CH=CH—NH—C | | N |
| I-276 | OH | Phenyl | Phenyl | Ethyl | OCH₃ | N | CH=CH—NH—C | | N |
| I-277 | OH | Phenyl | Phenyl | HO—CH₂ | CH₃ | N | CH=CH—NH—C | | N |
| I-278 | OH | Phenyl | Phenyl | HO—CH₂ | OCH₃ | N | CH=CH—NH—C | | N |
| I-279 | OH | Phenyl | Phenyl | Methyl | CH₃ | N | N=CH—NH—C | | N |
| I-280 | OH | Phenyl | Phenyl | Ethyl | CH₃ | N | N=CH—NH—C | | N |
| I-281 | OH | Phenyl | Phenyl | Propyl | CH₃ | N | N=CH—NH—C | | N |
| I-282 | OH | Phenyl | Phenyl | HO—CH₂—CH₂ | CH₃ | N | N=CH—NH—C | | N |
| I-283 | OH | Phenyl | Phenyl | Phenyl-CH₂—CH₂ | CH₃ | N | N=CH—NH—C | | N |
| I-284 | OH | Phenyl | Phenyl | Phenyl-CH₂—CH₂—CH₂ | CH₃ | N | N=CH—NH—C | | N |
| I-285 | OH | Phenyl | Phenyl | 4-Me-Phenyl-CH₂—CH₂ | CH₃ | N | N=CH—NH—C | | N |
| I-286 | OH | Phenyl | Phenyl | Methyl | CH₃ | N | O—CH₂—CH₂—C | | N |
| I-287 | OH | Phenyl | Phenyl | Ethyl | CH₃ | N | O—CH₂—CH₂—C | | N |
| I-288 | OH | Phenyl | Phenyl | HO—CH₂ | CH₃ | N | O—CH₂—CH₂—C | | N |
| I-289 | OH | Phenyl | Phenyl | HO—CH₂—CH₂ | CH₃ | N | O—CH₂—CH₂—C | | N |
| I-290 | OH | Phenyl | Phenyl | Phenyl-CH₂—CH₂ | CH₃ | N | O—CH₂—CH₂—C | | N |
| I-291 | OH | Phenyl | Phenyl | Phenyl-CH₂—CH₂ | CH₃ | N | CH₂—CH₂—O—C | | N |
| I-292 | OH | Phenyl | Phenyl | Methyl | CH₃ | N | CH₂—CH₂—O—C | | N |
| I-293 | OH | Phenyl | Phenyl | Ethyl | CH₃ | N | CH₂—CH₂—O—C | | N |
| I-294 | OH | Phenyl | Phenyl | Ethyl | CH₃ | N | CH₂—CH₂—CH₂—C | | N |
| I-295 | OH | Phenyl | Phenyl | Ethyl | OCH₃ | N | CH₂—CH₂—CH₂—C | | N |
| I-296 | OH | Phenyl | Phenyl | Methyl | CH₃ | N | CH₂—CH₂—CH₂—C | | N |
| I-297 | OH | Phenyl | Phenyl | Methyl | OCH₃ | N | CH₂—CH₂—CH₂—C | | N |
| I-298 | OH | Phenyl | Phenyl | HO—CH₂ | CH₃ | N | CH₂—CH₂—CH₂—C | | N |
| I-299 | OH | Phenyl | Phenyl | HO—CH₂—CH₂ | CH₃ | N | CH₂—CH₂—CH₂—C | | N |
| I-300 | OH | Phenyl | Phenyl | Phenyl-CH₂—CH₂ | CH₃ | N | CH₂—CH₂—CH₂—C | | N |
| I-301 | OH | Phenyl | Phenyl | 4-MeO-Phenyl-CH₂—CH₂—CH₂ | CH₃ | N | CH₂—CH₂—CH₂—C | | N |
| I-302 | OH | 2-Naphthyl | Phenyl | Methyl | OCH₃ | N | OCH₃ | CH | N |
| I-303 | OH | 2-Naphthyl | Phenyl | Methyl | CH₃ | N | CH₃ | CH | N |
| I-304 | OH | 2-Naphthyl | Phenyl | Methyl | OCH₃ | N | CH₃ | CH | N |
| I-305 | OH | 2-Naphthyl | Phenyl | Methyl | CH₃ | N | OCH₃ | CH | N |
| I-306 | OH | 2-Naphthyl | Phenyl | Methyl | Ethyl | N | CH₃ | CH | N |

TABLE 1-continued

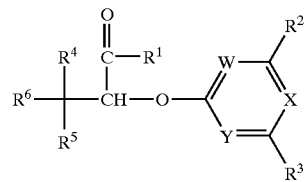

I

| No. | R¹ | R⁴ | R⁵ | R⁶ | R² | X | R³ | Y | W |
|---|---|---|---|---|---|---|---|---|---|
| I-307 | OH | 2-Naphthyl | Phenyl | Ethyl | OCH₃ | N | OCH₃ | CH | N |
| I-308 | OH | 2-Naphthyl | Phenyl | Ethyl | CH₃ | N | CH₃ | CH | N |
| I-309 | OH | 2-Naphthyl | Phenyl | Ethyl | OCH₃ | N | CH₃ | CH | N |
| I-310 | OH | 2-Naphthyl | Phenyl | Ethyl | CH₃ | N | OCH₃ | CH | N |
| I-311 | OH | 2-Naphthyl | Phenyl | Ethyl | Ethyl | N | CH₃ | CH | N |
| I-312 | OH | 2-Naphthyl | Phenyl | Propyl | CH₃ | N | CH₃ | CH | N |
| I-313 | OH | 2-Naphthyl | Phenyl | Propyl | OCH₃ | N | CH₃ | CH | N |
| I-314 | OH | 2-Naphtyl [sic] | Phenyl | HO—CH₂ | CH₃ | N | CH₃ | CH | N |
| I-315 | OH | 2-Naphtyl [sic] | Phenyl | HO—CH₂ | OCH₃ | N | CH₃ | CH | N |
| I-316 | OH | 2-Naphtyl [sic] | Phenyl | HO—CH₂ | OCH₃ | N | OCH₃ | CH | N |
| I-317 | OH | 2-Naphtyl [sic] | Phenyl | HO—CH₂—CH₂ | OCH₃ | N | OCH₃ | CH | N |
| I-318 | OH | 2-Naphtyl [sic] | Phenyl | HO—CH₂—CH₂ | CH₃ | N | CH₃ | CH | N |
| I-319 | OH | 2-Naphtyl [sic] | Phenyl | HO—CH₂—CH₂ | OCH₃ | N | CH₃ | CH | N |
| I-320 | OH | 2-Naphtyl [sic] | Phenyl | p-Me-Phenyl-CH₂—CH₂ | CH₃ | N | CH₃ | CH | N |
| I-321 | OH | 2-Naphtyl [sic] | Phenyl | p-Me-Phenyl-CH₂—CH₂ | OCH₃ | N | CH₃ | CH | N |
| I-322 | OH | 2-Naphtyl [sic] | Phenyl | p-MeO-Phenyl-CH₂—CH₂ | CH₃ | N | OCH₃ | CH | N |
| I-323 | OH | 2-Naphtyl [sic] | Phenyl | p-MeO-Phenyl-CH₂—CH₂ | CH₃ | N | CH₃ | CH | N |
| I-324 | OH | 2-Naphtyl [sic] | Phenyl | p-Me-Phenyl-CH₂—CH₂—CH₂ | CH₃ | N | CH₃ | CH | N |
| I-325 | OH | 2-Naphtyl [sic] | Phenyl | p-Me-Phenyl-CH₂—CH₂—CH₂ | OCH₃ | N | CH₃ | CH | N |
| I-326 | OH | 2-Naphtyl [sic] | Phenyl | p-MeO-Phenyl-CH₂—CH₂—CH₂ | CH₃ | N | CH₃ | CH | N |
| I-327 | OH | 2-Naphtyl [sic] | Phenyl | p-MeO-Phenyl-CH₂—CH₂—CH₂ | OCH₃ | N | CH₃ | CH | N |
| I-328 | OH | 2-Naphtyl [sic] | Phenyl | p-MeO-Phenyl-CH₂—CH₂—CH₂ | CH₃ | N | OCH₃ | CH | N |
| I-329 | OH | 2-Naphtyl [sic] | Phenyl | p-MeO-Phenyl-CH₂—CH₂—CH₂ | CH₃ | CH | CH₃ | N | N |
| I-330 | OH | 2-Naphtyl [sic] | Phenyl | p-MeO-Phenyl-CH₂—CH₂—CH₂ | OCH₃ | CH | CH₃ | N | N |
| I-331 | OH | 2-Naphtyl [sic] | Phenyl | p-MeO-Phenyl-CH₂—CH₂—CH₂ | OCH₃ | CH | OCH₃ | N | N |
| I-332 | OH | 2-Naphtyl [sic] | Phenyl | p-MeO-Phenyl-CH₂—CH₂—CH₂ | CH₂—CH₂—CH₂—C | | CH₃ | N | N |
| I-333 | OH | 2-Naphtyl [sic] | Phenyl | p-MeO-Phenyl-CH₂—CH₂—CH₂ | CH₂—CH₂—CH₂—C | | H | N | N |
| I-334 | OH | 2-Naphtyl [sic] | Phenyl | p-MeO-Phenyl-CH₂—CH₂—CH₂ | CH₂—CH₂—CH₂—C | | OCH₃ | N | N |
| I-335 | OH | 2-Naphtyl [sic] | Phenyl | p-Me-Phenyl-CH₂—CH₂—CH₂ | CH₂—CH₂—CH₂—C | | CH₃ | N | N |
| I-336 | OH | 2-Naphtyl [sic] | Phenyl | p-Me-Phenyl-CH₂—CH₂—CH₂ | CH₂—CH₂—CH₂—C | | H | N | N |
| I-337 | OH | 2-Naphtyl [sic] | Phenyl | p-Me-Phenyl-CH₂—CH₂—CH₂ | CH₂—CH₂—CH₂—C | | OCH₃ | N | N |
| I-338 | OH | 2-Naphtyl [sic] | Phenyl | HO—CH₂—CH₂ | CH₂—CH₂—CH₂—C | | CH₃ | N | N |
| I-339 | OH | 2-Naphtyl [sic] | Phenyl | HO—CH₂—CH₂ | CH₂—CH₂—CH₂—C | | H | N | N |
| I-340 | OH | 2-Naphtyl [sic] | Phenyl | HO₂C—CH₂ | CH₂—CH₂—CH₂—C | | CH₃ | N | N |
| I-341 | OH | 2-Naphtyl [sic] | Phenyl | HO₂C—CH₂ | CH₂—CH₂—CH₂—C | | H | N | N |
| I-342 | OH | 2-Naphtyl [sic] | Phenyl | Methyl | CH₂—CH₂—CH₂—C | | CH₃ | N | N |
| I-343 | OH | 2-Naphtyl [sic] | Phenyl | Methyl | CH₂—CH₂—CH₂—C | | H | N | N |
| I-344 | OH | 2-Naphtyl [sic] | Phenyl | Ethyl | CH₂—CH₂—CH₂—C | | CH₃ | N | N |
| I-345 | OH | 2-Naphtyl [sic] | Phenyl | Ethyl | CH₂—CH₂—CH₂—C | | H | N | N |
| I-346 | OH | 2-Naphtyl [sic] | Phenyl | Ethyl | CH₃ | CH | CH₃ | N | N |
| I-347 | OH | 2-Naphtyl [sic] | Phenyl | Ethyl | OCH₃ | CH | CH₃ | N | N |
| I-348 | OH | 2-Naphtyl [sic] | Phenyl | Ethyl | Ethyl | CH | CH₃ | N | N |
| I-349 | OH | 2-Naphtyl [sic] | Phenyl | Ethyl | OCH₃ | CH | OCH₃ | N | N |
| I-350 | OH | 2-Naphtyl [sic] | Phenyl | Methyl | CH₃ | CH | CH₃ | N | N |
| I-351 | OH | 2-Naphtyl [sic] | Phenyl | Methyl | OCH₃ | CH | CH₃ | N | N |
| I-352 | OH | 2-Naphtyl [sic] | Phenyl | Methyl | OCH₃ | CH | OCH₃ | N | N |
| I-353 | OH | 2-Naphtyl [sic] | Phenyl | HO—CH₂ | CH₃ | CH | CH₃ | N | N |
| I-354 | OH | 2-Naphtyl [sic] | Phenyl | HO—CH₂ | OCH₃ | CH | CH₃ | N | N |

TABLE 1-continued

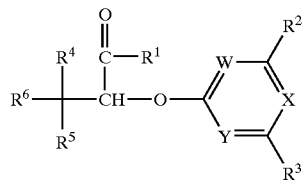

| No. | R¹ | R⁴ | R⁵ | R⁶ | R² | X | R³ | Y | W |
|---|---|---|---|---|---|---|---|---|---|
| I-355 | OH | 2-Naphtyl [sic] | Phenyl | HO—CH₂ | OCH₃ | CH | OCH₃ | N | N |
| I-356 | OH | 2-Naphtyl [sic] | Phenyl | HO—CH₂ | Ethyl | CH | CH₃ | N | N |
| I-357 | OH | 2-Naphtyl [sic] | Phenyl | HO—CH₂—CH₂ | CH₃ | CH | CH₃ | N | N |
| I-358 | OH | 2-Naphtyl [sic] | Phenyl | HO—CH₂—CH₂ | OCH₃ | CH | CH₃ | N | N |
| I-359 | OH | 2-Naphtyl [sic] | Phenyl | HO—CH₂—CH₂ | OCH₃ | CH | OCH₃ | N | N |
| I-360 | OH | 2-Naphtyl [sic] | Phenyl | HO₂C—CH₂ | CH₃ | CH | CH₃ | N | N |
| I-361 | OH | 2-Naphtyl [sic] | Phenyl | HO₂C—CH₂ | OCH₃ | CH | CH₃ | N | N |
| I-362 | OH | 2-Naphtyl [sic] | Phenyl | HO₂C—CH₂ | OCH₃ | CH | CH₃ | N | N |
| I-363 | OH | 2-Naphtyl [sic] | Phenyl | p-Me-Phenyl-CH₂—CH₂ | CH₃ | CH | CH₃ | N | N |
| I-364 | OH | 2-Naphtyl [sic] | Phenyl | p-Me-Phenyl-CH₂—CH₂ | OCH₃ | CH | CH₃ | N | N |
| I-365 | OH | 2-Naphtyl [sic] | Phenyl | p-Me-Phenyl-CH₂—CH₂ | OCH₃ | CH | OCH₃ | N | N |
| I-366 | OH | 2-Naphtyl [sic] | Phenyl | p-Me-Phenyl-CH₂—CH₂—CH₂ | CH₃ | CH | CH₃ | N | N |
| I-367 | OH | 2-Naphtyl [sic] | Phenyl | p-Me-Phenyl-CH₂—CH₂—CH₂ | OCH₃ | CH | CH₃ | N | N |
| I-368 | OH | 2-Naphtyl [sic] | Phenyl | p-Me-Phenyl-CH₂—CH₂—CH₂ | OCH₃ | CH | OCH₃ | N | N |
| I-369 | OH | 2-Naphtyl [sic] | Phenyl | p-MeO-Phenyl-CH₂—CH₂—CH₂ | CH₃ | CH | CH₃ | N | N |
| I-370 | OH | 2-Naphtyl [sic] | Phenyl | p-MeO-Phenyl-CH₂—CH₂—CH₂ | OCH₃ | CH | CH₃ | N | N |
| I-371 | OH | 2-Naphtyl [sic] | Phenyl | p-MeO-Phenyl-CH=CH₂—CH₂ | CH₃ | CH | CH₃ | N | N |
| I-372 | OH | 2-Naphtyl [sic] | Phenyl | p-MeO-Phenyl-CH=CH₂—CH₂ | OCH₃ | CH | CH₃ | N | N |
| I-373 | OH | 1-Naphtyl [sic] | Phenyl | p-MeO-Phenyl-CH=CH₂—CH₂ | CH₃ | CH | CH₃ | N | N |
| I-374 | OH | 1-Naphtyl [sic] | Phenyl | p-MeO-Phenyl-CH=CH₂—CH₂ | OCH₃ | CH | CH₃ | N | N |
| I-375 | OH | 1-Naphtyl [sic] | Phenyl | p-MeO-Phenyl-CH=CH₂—CH₂ | OCH₃ | CH | OCH₃ | N | N |
| I-376 | OH | 1-Naphtyl [sic] | Phenyl | p-MeO-Phenyl-CH₂—CH₂—CH₂ | CH₃ | CH | CH₃ | N | N |
| I-377 | OH | 1-Naphtyl [sic] | Phenyl | p-MeO-Phenyl-CH₂—CH₂—CH₂ | OCH₃ | CH | CH₃ | N | N |
| I-378 | OH | 1-Naphtyl [sic] | Phenyl | p-MeO-Phenyl-CH₂—CH₂—CH₂ | OCH₃ | CH | OCH₃ | N | N |
| I-379 | OH | 1-Naphtyl [sic] | Phenyl | Phenylmethyl-O—CH₂ | CH₃ | CH | CH₃ | N | N |
| I-380 | OH | 1-Naphtyl [sic] | Phenyl | Phenylmethyl-O—CH₂ | OCH₃ | CH | CH₃ | N | N |
| I-381 | OH | 1-Naphtyl [sic] | Phenyl | HO—CH₂ | CH₃ | CH | CH₃ | N | N |
| I-382 | OH | 1-Naphtyl [sic] | Phenyl | HO—CH₂ | OCH₃ | CH | CH₃ | N | N |
| I-383 | OH | 1-Naphtyl [sic] | Phenyl | HO—CH₂—CH₂ | CH₃ | CH | CH₃ | N | N |
| I-384 | OH | 1-Naphtyl [sic] | Phenyl | HO—CH₂—CH₂ | OCH₃ | CH | CH₃ | N | N |
| I-385 | OH | 1-Naphtyl [sic] | Phenyl | Propyl | CH₃ | CH | CH₃ | N | N |
| I-386 | OH | 1-Naphtyl [sic] | Phenyl | Propyl | OCH₃ | CH | CH₃ | N | N |
| I-387 | OH | 1-Naphtyl [sic] | Phenyl | Ethyl | OCH₃ | CH | OCH₃ | N | N |
| I-388 | OH | 1-Naphtyl [sic] | Phenyl | Ethyl | OCH₃ | CH | CH₃ | N | N |
| I-389 | OH | 1-Naphtyl [sic] | Phenyl | Ethyl | CH₃ | CH | CH₃ | N | N |
| I-390 | OH | 1-Naphtyl [sic] | Phenyl | Methyl | CH₃ | CH | CH₃ | N | N |
| I-391 | OH | 1-Naphtyl [sic] | Phenyl | Methyl | OCH₃ | CH | CH₃ | N | N |
| I-392 | OH | 1-Naphtyl [sic] | Phenyl | Methyl | OCH₃ | CH | OCH₃ | N | N |
| I-393 | OH | 3,4-Dioxomethyl-enylphenyl [sic] | Phenyl | Methyl | CH₃ | CH | CH₃ | N | N |
| I-394 | OH | 3,4-Dioxomethyl-enylphenyl [sic] | Phenyl | Methyl | OCH₃ | CH | CH₃ | N | N |
| I-395 | OH | 3,4-Dioxomethyl-enylphenyl [sic] | Phenyl | Methyl | OCH₃ | CH | OCH₃ | N | N |
| I-396 | OH | 3,4-Dioxomethyl-enylphenyl [sic] | Phenyl | Ethyl | CH₃ | CH | CH₃ | N | N |
| I-397 | OH | 3,4-Dioxomethyl-enylphenyl [sic] | Phenyl | Ethyl | OCH₃ | CH | CH₃ | N | N |

TABLE 1-continued

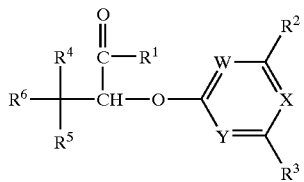

| No. | R$^1$ | R$^4$ | R$^5$ | R$^6$ | R$^2$ | X | R$^3$ | Y | W |
|---|---|---|---|---|---|---|---|---|---|
| I-398 | OH | 3,4-Dioxomethyl-enylphenyl [sic] | Phenyl | Ethyl | OCH$_3$ | CH | OCH$_3$ | N | N |
| I-399 | OH | 3,4-Dioxomethyl-enylphenyl [sic] | Phenyl | HO—CH$_2$ | CH$_3$ | CH | CH$_3$ | N | N |
| I-400 | OH | 3,4-Dioxomethyl-enylphenyl [sic] | Phenyl | HO—CH$_2$ | OCH$_3$ | CH | CH$_3$ | N | N |
| I-401 | OH | 3,4-Dioxomethyl-enylphenyl [sic] | Phenyl | HO—CH$_2$—CH$_2$ | CH$_3$ | CH | CH$_3$ | N | N |
| I-402 | OH | 3,4-Dioxomethyl-enylphenyl [sic] | Phenyl | HO—CH$_2$—CH$_2$ | OCH$_3$ | CH | CH$_3$ | N | N |
| I-403 | OH | 3,4-Dioxomethyl-enylphenyl [sic] | Phenyl | p-Me-Phenyl-CH$_2$—CH$_2$—CH$_2$ | CH$_3$ | CH | CH$_3$ | N | N |
| I-404 | OH | 3,4-Dioxomethyl-enylphenyl [sic] | Phenyl | p-Me-Phenyl-CH$_2$—CH$_2$—CH$_2$ | OCH$_3$ | CH | CH$_3$ | N | N |
| I-405 | OH | 3,4-Dioxomethyl-enylphenyl [sic] | Phenyl | p-MeO-Phenyl-CH$_2$—CH$_2$—CH$_2$ | CH$_3$ | CH | CH$_3$ | N | N |
| I-406 | OH | 3,4-Dioxomethyl-enylphenyl [sic] | Phenyl | p-MeO-Phenyl-CH$_2$—CH$_2$—CH$_2$ | OCH$_3$ | CH | CH$_3$ | N | N |
| I-407 | OH | 3,4-Dioxomethyl-enylphenyl [sic] | Phenyl | p-MeO-Phenyl-CH$_2$—CH$_2$—CH$_2$ | OCH$_3$ | CH | OCH$_3$ | N | N |

We claim:

1. An α-hydroxy carboxylic acid compound of the formula I

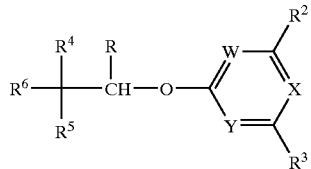

where R is a group

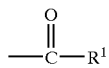

where R$^1$ has the following meanings:
b) a succinylimidoxy group
c) a 5-membered heteroaromatic ring selected from the group consisting of pyrrolyl, pyrazolyl, imidazolyl and triazolyl, which ring is bonded to CH via a ring nitrogen atom and which may carry one or two halogen atoms or one or two C$_1$–C$_4$-alkyl or one or two C$_1$–C$_4$-alkoxy groups;
d) a group

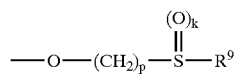

where k can assume the values 0, 1 and 2, p can assume the values 1, 2, 3 and 4, and R$^9$ is C$_1$–C$_4$-alkyl, C$_3$–C$_7$-cycloalkyl, C$_3$–C$_6$-alkenyl, C$_3$–C$_6$-alkynyl or unsubstituted or substituted phenyl which can be substituted by one or more of the following radicals: halogen, nitro, cyano, C$_1$–C$_4$-alkyl, C$_1$–C$_4$-haloalkyl, hydroxyl, C$_1$–C$_4$-alkoxy, C$_1$–C$_4$-alkylthio, mercapto, amino, C$_1$–C$_4$-alkylamino, C$_1$–C$_4$-dialkylamino;

e) a radical OR$^{10}$, where R$^{10}$ is:
hydrogen, the cation of an alkali metal lithium, sodium, potassium or the cation of an alkaline earth metal calcium, magnesium and barium, and physiologically tolerated alkylammonium ion or the ammonium ion;
C$_3$–C$_8$-cycloalkyl,
C$_1$–C$_8$-alkyl,
CH$_2$ phenyl which can be substituted on the phenyl radical by one or more of the following radicals: halogen, nitro, cyano, C$_1$–C$_4$-alkyl, C$_1$–C$_4$-haloalkyl, hydroxyl, C$_1$–C$_4$-alkoxy, mercapto, C$_1$–C$_4$-alkylthio, amino, C$_1$–C$_4$-alkylamino, C$_1$–C$_4$-dialkylamino, a C$_3$–C$_6$-alkenyl or C$_3$–C$_6$-alkynyl group, it being possible for this group in turn to carry one to five halogen atoms;
a phenyl radical which can carry one to five halogen atoms and/or one to three of the following radicals: nitro, cyano, C$_1$–C$_4$-alkyl, C$_1$–C$_4$-haloalkyl, hydroxyl, C$_1$–C$_4$-alkoxymercapto, C$_1$–C$_4$-alkylthio, amino, C$_1$–C$_4$-alkylamino, C$_1$–C$_4$-dialkylamino;
a 5-membered heteroaromatic system which is linked via a nitrogen atom and has one to three nitrogen atoms, and which may carry one or two halogen atoms and/or one or two of the following radicals: C$_1$–C$_4$-alkyl, C$_1$–C$_4$-haloalkyl, C$_1$–C$_4$-alkoxy, phenyl, C$_1$–C$_4$-haloalkoxy and/or C$_1$–C$_4$-alkylthio;

f) a radical

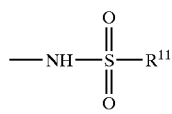

where $R^{11}$ is:
  $C_1$–$C_4$-alkyl, $C_3$–$C_6$-alkenyl, $C_3$–$C_6$-alkynyl, $C_3$–$C_8$-cycloalkyl, it being possible for these radicals to carry a $C_1$–$C_4$-alkoxy, $C_1$–$C_4$-alkylthio, and/or a phenyl radical;
  phenyl which is unsubstituted or substituted by one or more members selected from the group consisting of halogen, nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $C_1$–$C_4$-alkylamino, and $C_1$–$C_4$-dialkylamino;

h)

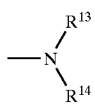

where $R^{13}$ and $R^{14}$ can be identical or different and have the following meanings: hydrogen, $C_1$–$C_7$-alkyl, $C_3$–$C_7$-cycloalkyl, $C_3$–$C_7$-alkenyl, $C_3$–$C_7$-alkynyl, benzyl, phenyl, wherein the phenyl radicals are optionally unsubstituted or substituted by one or more members selected from the group consisting of halogen, nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $C_1$–$C_4$-alkylamino, and $C_1$–$C_4$-dialkylamino,
or $R^{13}$ and $R^{14}$ together form a $C_4$–$C_7$-alkylene chain which is closed to a ring, is unsubstituted or substituted by $C_1$–$C_4$-alkyl and may contain a hetero atom selected from the group consisting of oxygen, sulfur or nitrogen,
or R is tetrazolyl or cyano;
W is nitrogen, C—$NO_2$, a CH group when one or more of the substituents $R^2$, $R^3$, $R^{15}$ and/or $R^{16}$ are a nitro group, or when X and/or Y are nitrogen;
$R^2$ and $R^3$ are phenyl, optionally substituted once to three times by halogen, hydroxyl, amino, mono- or dialkyl ($C_1$–$C_3$)-amino, $C_1$–$C_3$-alkyl, $C_1$–$C_3$-alkoxy, mercapto or $C_1$–$C_3$-alkylthio, carboxyl or $C_1$–$C_3$-alkylcarboxyl;
X is nitrogen or $CR^{15}$ where $R^{15}$ is hydrogen or $C_1$–$C_5$-alkyl, optionally substituted once or twice by hydroxyl or carboxyl; $C_1$–$C_6$-alkoxy, $C_1$–$C_6$-alkylthio, phenyl, benzyl, hydroxyl, mercapto, nitro, amino, $C_1$–$C_4$-alkylamino, $C_1$–$C_4$-dialkylamino, cyano or carboxyl;
it is furthermore possible for $CR^{15}$ to be linked to $R^2$ to give a 5- or 6-membered ring as described above, or $CR^{15}$ can form with $R^3$ and its adjacent carbon atom a 5- or 6-membered alkylene or alkylidene ring in each of nitrogen, oxygen or sulfur, and the 5- or 6-membered ring may optionally be substituted once to three times by the following radicals:
halogen, nitro, cyano, hydroxyl, mercapto, $C_1$–$C_3$-alkyl, $C_1$–$C_3$-haloalkyl, $C_1$–$C_3$-alkoxy, $C_1$–$C_3$-alkylthio, amino, $C_1$–$C_3$-alkylamino, $C_1$–$C_3$-dialkylamino or carboxyl; nitrogen in the 5-membered ring may also be substituted by a formyl or acetyl group;
Y is nitrogen or $CR^{16}$ where $R^{16}$ is hydrogen, $C_1$–$C_5$-alkyl, $C_1$–$C_5$-alkoxy, $C_1$–$C_5$-alkylthio, nitro, phenyl, hydroxyl, halogen, cyano, amino, $C_1$–$C_4$-alkylamino, $C_1$–$C_4$-dialkylamino, mercapto or carboxyl, or $R^{16}$ forms together with $R^3$ and its adjacent carbon atom a 5- or 6-membered ring as described above wherein two of X, Y and W are nitrogen and the other is carbon;
$R^4$ is phenyl, naphthyl, dihydro- or tetrahydronaphthyl, which can be substituted by one or more of the following radicals: halogen, nitro, cyano, hydroxyl, $C_1$–$C_4$-alkyl, $C_1$–$C_4$-haloalkyl, $C_1$–$C_4$-alkoxy, $C_1$–$C_4$-haloalkoxy, phenoxy, phenyl, $C_1$–$C_4$-alkylthio, amino, $C_1$–$C_4$-alkylamino or $C_1$–$C_4$-dialkylamino, it being possible for two radicals on adjacent carbon atoms to form, together with the latter, a five- or six-membered ring which is linked by an alkylene or alkylidene group and in which one or more methylene or methylidene groups can be replaced by oxygen;
$R^5$ can have the same meanings as $R^4$, it being possible for $R^4$ and $R^5$ to be identical or different; and
$R^6$ is hydrogen, $C_1$–$C_8$-alkyl, $C_3$–$C_8$-alkenyl or $C_3$–$C_8$-alkynyl, it being possible for each of these radicals to be substituted one or more times by: halogen, nitro, cyano, $C_1$–$C_4$-alkoxy, hydroxyl, $C_1$–$C_4$-alkylthio, mercapto, $C_1$–$C_4$-haloalkoxy, carboxyl, $C_1$–$C_4$-alkylcarboxy, $C_1$–$C_4$-alkylcarbonyl, amino, $C_1$–$C_4$-alkylamino, $C_1$–$C_4$-dialkylamino, a five- or six-membered heteroaromatic system which has one to three nitrogen atoms and/or one sulfur or oxygen atom and which can carry one to four halogen atoms and/or one or two of the following radicals; $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, phenyl, phenoxy or phenylcarbonyl, it being possible for the phenyl radicals in turn to carry one to five halogen atoms and/or one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio; phenyl, naphthyl, which can in turn be substituted one or more times by: halogen, nitro, cyano, hydroxyl, $C_1$–$C_4$-alkoxy, $C_1$–$C_4$-alkyl, $C_1$–$C_4$-haloalkyl, $C_1$–$C_4$-haloalkoxy, mercapto, $C_1$–$C_4$-alkylthio, amino, $C_1$–$C_4$-alkylamino, $C_1$–$C_4$-dialkyl amino or phenoxy; or one of the following radicals:

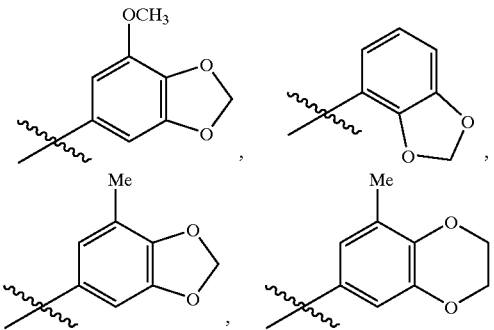

2. An α-hydroxy carboxylic acid derivative as claimed in claim 1, wherein R is COOH.

3. An α-hydroxy carboxylic acid compound as claimed in claim 1, wherein at least one of the radicals $R^4$ and $R^5$ is phenyl.

4. An α-hydroxy carboxylic acid compound as claimed in claim 3, wherein $R^4$ and $R^5$ are both phenyl.

5. An α-hydroxy carboxylic acid compound as claimed in claim 1, wherein $R^6$ is $C_1$–$C_8$-alkyl, unsubstituted or substituted by OH or $C_1$–$C_4$-alkoxy.

6. An α-hydroxy carboxylic acid compound as claimed in claim 1, wherein X is CH.

7. A method of treating hypertension, pulmonary hypertension, acute and chronic kidney failure, chronic heart failure, cerebral ischemia, restenosis after angioplasty and prostate cancer, which method comprises administering to a patient in need of such treatment a therapeutically effective amount of an α-hydroxy carboxylic acid compound of the formula I, as defined in claim 1.

8. A method for inducing endothelin receptor-antagonizing activity which comprises administering a therapeutically effective amount of a compound as defined in claim 1 to a host in need of endothelin receptor-antagonizing activity.

* * * * *